US012708729B2

(12) United States Patent
Walvekar

(10) Patent No.: US 12,708,729 B2
(45) Date of Patent: Aug. 18, 2026

(54) TRACHEOSTOMY ACCESSORY AND METHODS OF USE

(71) Applicant: The Board of Supervisors of Louisiana State University and Agricultural and Mechanical College, Baton Rouge, LA (US)

(72) Inventor: Rohan R. Walvekar, Metairie, LA (US)

(73) Assignee: THE BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 793 days.

(21) Appl. No.: 17/920,721

(22) PCT Filed: Apr. 21, 2021

(86) PCT No.: PCT/US2021/028387

§ 371 (c)(1),
(2) Date: Oct. 21, 2022

(87) PCT Pub. No.: WO2021/216700

PCT Pub. Date: Oct. 28, 2021

(65) Prior Publication Data

US 2023/0166067 A1 Jun. 1, 2023

Related U.S. Application Data

(60) Provisional application No. 63/013,855, filed on Apr. 22, 2020.

(51) Int. Cl.
*A61M 16/04* (2006.01)

(52) U.S. Cl.
CPC ...... *A61M 16/0497* (2013.01); *A61M 16/047* (2013.01)

(58) Field of Classification Search
CPC ............ A61M 16/0465; A61M 16/047; A61M 16/0488; A61M 16/0497
See application file for complete search history.

(56) References Cited

U.S. PATENT DOCUMENTS 2,923,299 A * 2/1960 Blackwood ....... A61M 16/0465 128/207.17
3,286,713 A * 11/1966 Kurtz ................ A61F 13/01021 128/207.14

(Continued)

FOREIGN PATENT DOCUMENTS

CN 110237388 A * 9/2019 .......... A61M 16/047
DE 202014002957 U1 * 5/2014 .......... A61M 16/047

(Continued)

OTHER PUBLICATIONS

International Search Report and Written Opinion for PCT/US2021/028387 mailed Aug. 6, 2021.

*Primary Examiner* — Kathryn E Ditmer
(74) *Attorney, Agent, or Firm* — Baker, Donelson, Bearman, Caldwell & Berkowitz, PC

(57) ABSTRACT

The present invention is directed to a tracheostomy accessory and an associated kit to improve patient comfort and promote stomal healing. A tracheostomy accessory that comprises a faceplate. The faceplate comprises a central portion, a least two end sections, and at least two linking sections. The linking sections can be configured to connect the central portion to the end sections. A method of use of the tracheostomy accessory is also disclosed herein.

22 Claims, 21 Drawing Sheets

(56) References Cited

U.S. PATENT DOCUMENTS

| | | | | | |
|---|---|---|---|---|---|
| 3,422,817 | A * | 1/1969 | Mishkin | A61M 25/02 | 128/207.14 |
| 3,585,997 | A * | 6/1971 | Ancerewicz, Jr. | A61M 16/047 | 604/338 |
| 4,033,353 | A * | 7/1977 | La Rosa | A61M 16/0497 | 128/207.15 |
| 4,235,229 | A * | 11/1980 | Ranford | A61M 16/0497 | 128/207.15 |
| 4,530,354 | A * | 7/1985 | Froilan | A61M 25/02 | 128/207.17 |
| 5,361,754 | A * | 11/1994 | Stuart | A61M 16/0497 | 128/DIG. 26 |
| 5,626,132 | A * | 5/1997 | Miller | A61F 2/20 | 128/207.14 |
| 5,782,236 | A * | 7/1998 | Ess | A61M 25/02 | 24/339 |
| 5,819,734 | A * | 10/1998 | Deily | A61M 16/0465 | 128/911 |
| 6,009,872 | A * | 1/2000 | Delaplane | A61M 16/0488 | 128/912 |
| 6,029,668 | A * | 2/2000 | Freed | A61B 1/00154 | 128/207.14 |
| 6,050,263 | A * | 4/2000 | Choksi | A61M 16/0488 | 128/207.14 |
| 6,067,985 | A * | 5/2000 | Islava | A61M 16/0488 | 128/207.14 |
| 7,093,598 | B1 * | 8/2006 | Hanneman | A61M 16/047 | 128/207.14 |
| 8,739,796 | B2 | 6/2014 | Kiernan et al. | | |
| 9,788,583 | B1 * | 10/2017 | Owens | A41D 13/1245 | |
| 10,894,138 | B2 | 1/2021 | Bateman et al. | | |
| 2004/0226564 | A1 * | 11/2004 | Persson | A61M 16/0465 | 128/207.14 |
| 2005/0092328 | A1 * | 5/2005 | Herrick | A61M 16/0497 | 128/207.17 |
| 2005/0166924 | A1 * | 8/2005 | Thomas | A61M 16/0429 | 128/207.14 |
| 2009/0025730 | A1 * | 1/2009 | Pinel | A61M 16/047 | 128/207.15 |
| 2009/0320852 | A1 * | 12/2009 | Cuevas | A61M 16/0488 | 128/207.14 |
| 2011/0083672 | A1 | 4/2011 | Webster et al. | | |
| 2012/0048277 | A1 * | 3/2012 | Waldron | A61M 25/02 | 128/207.14 |
| 2012/0103342 | A1 | 5/2012 | Shikani et al. | | |
| 2012/0167893 | A1 * | 7/2012 | Schulz | A61M 16/0465 | 128/207.14 |
| 2012/0204882 | A1 * | 8/2012 | Hayman | A61M 16/0465 | 128/207.14 |
| 2012/0222682 | A1 * | 9/2012 | Nguyen | A61M 16/0497 | 128/207.17 |
| 2012/0247478 | A1 * | 10/2012 | Harrington | A61M 16/0825 | 128/207.14 |
| 2013/0025601 | A1 * | 1/2013 | Waldron | A61M 16/0497 | 128/207.14 |
| 2015/0320610 | A1 * | 11/2015 | Marsh | A61F 13/0203 | 604/385.01 |
| 2016/0235935 | A1 * | 8/2016 | Mirza | A61M 16/0463 | |
| 2017/0312150 | A1 * | 11/2017 | Kao | A61M 16/047 | |
| 2018/0043118 | A1 * | 2/2018 | Jeffrey | A61M 16/0825 | |
| 2018/0207381 | A1 * | 7/2018 | Winthrop | A61M 16/0497 | |
| 2020/0222649 | A1 | 7/2020 | Wilson et al. | | |

FOREIGN PATENT DOCUMENTS

| | | | | |
|---|---|---|---|---|
| GB | 2099306 | A * | 12/1982 | A61F 13/12 |
| GB | 2538860 | A * | 11/2016 | A61M 16/0497 |
| GB | 2544874 | A * | 5/2017 | A61M 16/047 |
| WO | WO-2019145669 | A1 * | 8/2019 | A61M 25/02 |

* cited by examiner

TRACHEOSTOMY ACCESSORY AND METHODS OF USE

CROSS-REFERENCE TO RELATED APPLICATIONS

This application claims priority from U.S. Provisional Application No. 63/013,855 filed on Apr. 22, 2020, the entire contents of which are incorporated herein by reference.

All patents, patent applications, and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

GOVERNMENT INTERESTS

Not applicable.

FIELD OF THE INVENTION

The present invention is directed to a tracheostomy accessory and kit, and associated methods for use of the accessory.

BACKGROUND OF THE INVENTION

There has been an increasing emphasis on quality improvement in terms of health care delivery globally and especially in the United States. For example, preventing hospital acquired injuries like tracheostomy associated pressure ulcers (TRAPUS) has a significant impact on hospital stay, infection control, quality of care and patient experience. Tracheostomy is a common procedure, often lifesaving, and is performed more to help more than 100,000 patients ever year. Inability to properly care of tracheostomy wounds, shear forces, pressure on the skin and moisture all impact the tracheostomy wound and consequently its care.

SUMMARY OF THE INVENTION

In one aspect, the present invention is directed to a tracheostomy accessory that comprises a faceplate. In embodiments, the faceplate comprises a central portion, a least two end sections, and at least two linking sections. The linking sections can be configured to connect the central portion to the end sections. In embodiments, the central portion is elevated in relation to the end sections such that contact between the faceplate and the skin of a patient is reduced. Each of the at least two end sections can comprise a footplate that is configured to support the faceplate on the patient. In certain embodiments, faceplate further comprising a cannula receiving portion with a hole, gap, notch, or channel extending through the central portion, wherein the cannula receiving portion is configured to receive and hold at least a portion of an outer tracheostomy cannula.

The linking sections can comprise a curvature that extends upward from the end sections and terminates at the central portion to create an arched faceplate. In embodiments, the central portion is integral with the linking sections, and each linking section is integral with one end section such that the faceplate comprises a single, continuous structure.

The faceplate can further comprise at least one stomal viewport comprising a hole, gap, notch, or channel extending through a portion of one of the linking sections. The stomal viewport can be configured to permit viewing of a stoma on the patient. The stomal view port can be further configured to permit care of the stoma. In embodiments, each linking section comprises a stomal view port.

The tracheostomy accessory can also comprise a wound dressing material configured to reside within a space between the skin of the patient and at least one linking section of the faceplate. In embodiments, the wound dressing material comprises a sponge. A central portion of the sponge can comprise a hole, gap, notch, or channel that is complementary to the cannula receiving portion of the faceplate and is configured to receive and hold at least a portion of the outer tracheostomy cannula. The sponge can comprise an adhesive material applied to at least a portion of the top or bottom surface of the sponge. The adhesive material, if present, is configured to reversibly secure the sponge to an undersurface or a top surface of the faceplate. In certain embodiments, at least a portion of the wound dressing material is configured to pass through the stomal view port. The dressing material can comprise a sponge with at least two protrusions. Each protrusions can be configured to pass through one of the stomal view ports. In embodiments, the dressing material comprises at least two sponges and the sponges are configured to reside within the space between the stomal viewports and the skin of the patient. In such embodiments, each sponge can be configured to reside on opposite sides of the outer tracheostomy cannula. An undersurface of the sponge can comprise an adhesive material configured to reversibly secure the sponge to the skin of the patient.

In certain embodiments, each footplate further comprises at least one cushion configured to reduce irritation of the patient's skin. A bottom surface of each footplate can comprise an area configured to receive and hold the at least one cushion. In embodiments, the cushion comprises a sleeve that is configured to cover at least a portion of one footplate.

In some embodiments, the faceplate further comprises at least one passthrough, notch, gap, hole, or ring that is configured to receive and hold a suture. The passthrough, notch, gap, hole, or ring can be disposed on the footplates. The faceplate can further comprise at least one means for attachment of a tracheostomy securing mechanism. The means for attachment of the tracheostomy securing mechanism can comprise a hole, gap, notch, or channel disposed on each footplate. In certain embodiments, the means for attachment of the tracheostomy securing mechanism is configured to prevent the tracheostomy securing mechanism from contacting the skin of the patient at the points where the tracheostomy securing mechanism is attached to the footplates. The tracheostomy securing mechanism can comprise a strap, string, cord, wire, or combination thereof configured to be secured around the neck of a patient. In embodiments, the tracheostomy securing means comprises a hook and loop fastener.

The cannula receiving portion of certain tracheostomy accessory embodiments further comprises a swivel adapter configured to permit the tracheostomy cannula and the faceplate to be adjusted as a single unit.

In embodiments, the faceplate comprises a medical grade metal, a medical-grade polymer, or a combination thereof. The medical grade metal can comprise stainless steel, titanium, tantalum, gold, platinum, palladium, or a combination thereof. In some embodiments, the faceplate comprises a silicone elastomer, sterilizable plastic, polytetrafluoroethylene, polyether block amide, polyvinyl chloride or a combination thereof. The tracheostomy accessory can comprise a faceplate that is reusable. In alternative embodiments, the faceplate is disposable.

In certain embodiments, the linking sections comprises a radius of curvature from about 30 degrees up to about 100 degrees. The linking sections can comprise a radius of curvature of about 35 degrees or about 90 degrees. The linking sections can comprise a mean angle of curvature from about 100 degrees to about 180 degrees. In some embodiments, the linking sections comprise a mean angle of curvature of about 125 degrees or about 161 degrees.

In embodiments, the faceplate comprises a height from about 3 mm to about 20 mm. The faceplate can comprise a height of about 5 mm or about 15 mm.

In another aspect, the present invention comprises a method of stabilizing a tracheostomy. The method can comprise obtaining the tracheostomy accessory in accordance with any one or more embodiments disclosed herein. The method can further include the step of placing the outer tracheostomy cannula through the cannula receiving portion of the faceplate and securing the faceplate to the patient.

In embodiments, the method further comprises the step of passing a wound dressing material through the stomal viewport. The faceplate can be secured to the patient via a strap, string, cord, wire, or combination thereof that is fastened around the patient's neck. The step of securing the faceplate to the patient can comprise passing at least one suture through the passthrough, notch, gap, hole, or ring and suturing the faceplate to the patient.

In another aspect, the present invention comprises a kit for use in stabilization of a tracheostomy tube. In embodiments, the kit comprises any of the various tracheostomy accessory embodiments disclosed herein. The kit can further comprise any of the various wound dressing material embodiments disclosed herein. The kit can also include instructions for use of the kit. In certain embodiments, the kit comprises a tracheostomy cannula.

Other objects and advantages of this invention will become readily apparent from the ensuing description.

BRIEF DESCRIPTION OF THE FIGURES

Certain illustrations, charts, or flow charts are provided to allow for a better understanding for the present invention. It is to be noted, however, that the drawings illustrate only selected embodiments of the inventions and are therefore not to be considered limiting of scope. Additional and equally effective embodiments and applications of the present invention exist.

DETAILED DESCRIPTION OF THE INVENTION

Abbreviations and Definitions

Figure 1:
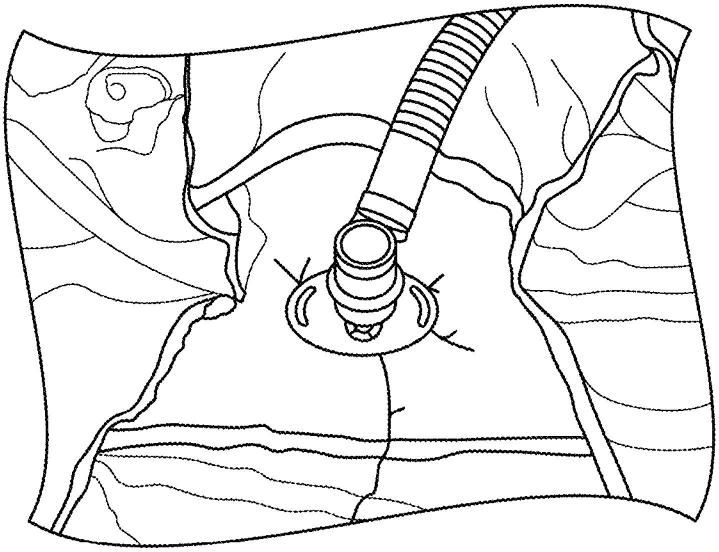
FIG. 1 shows a customary tracheostomy flange or faceplate design.

Detailed descriptions of one or more embodiments are provided herein. It is to be understood, however, that the present invention can be embodied in various forms. Therefore, specific details disclosed herein are not to be interpreted as limiting, but rather as a basis for the claims and as a representative basis for teaching one skilled in the art to employ the present invention in any appropriate manner.

The singular forms "a," "an," and "the" include plural reference unless the context clearly dictates otherwise. The use of the word "a" or "an" when used in conjunction with the term "comprising" in the claims and/or the specification can mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly, "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

The terms "comprising" and "including" and "having" and "involving" (and similarly "comprises," "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

For purposes of the present disclosure, it is noted that spatially relative terms, such as "up," "down," "right," "left," "beneath," "below," "lower," "above," "upper" and the like, can be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device can be otherwise oriented (rotated 90 degrees or at other orientations) and the spatially relative descriptors used herein interpreted accordingly.

The term "wound dressing material" and the like include, without limitation, any material or substance that absorbs drainage or exudate from a wound. The material can include, but is not limited to gauze, foam, packing strips, sponges, or any open-cell, absorbent, or porous material. The term includes any material that one having skill in the art would consider appropriate for packing wounds of various types, during various healing phases, and in various locations across or within the body.

The terms "subject" and "patient" as used herein include all members of the animal kingdom including, but not limited to, mammals, animals (e.g., cats, dogs, horses, swine, etc.) and humans.

The term "caretaker" as used herein refers to any person, group, or entity who has assumed responsibility to care for the subject or patient or to prepare the therapeutic device for use. By way of non-limiting example, a caretaker can include a physician, a nurse, a clinician, a pharmacist, a physician assistant, any employee of a clinical facility, a family member of the subject, a friend or acquaintance of the subject, an employee of the subject, or any other person, group, or entity who assumes responsibility to care for the subject. In certain instances, the subject can act as a caretaker, such as when tending to his or her own wounds.

The terms "faceplate" and "flange" are used interchangeably herein to refer to an accessory for use in securing a tracheostomy cannula to the neck of patient.

Description of Selected Embodiments

Disclosed herein is a tracheostomy accessory configured to improve patient comfort. The present invention is configured to minimize impact of the faceplate with the skin of the patient. Embodiments of the present invention prevent or reduce the accumulation of moisture around the stoma wounds created during a tracheostomy procedure. In various exemplary embodiments, the tracheostomy accessory improves the ability of health care professionals to inspect and care for stoma wounds. The tracheostomy accessory improves visibility of and access to the stoma wound. The tracheostomy accessory disclosed herein can provide for easy dressing changes while avoiding drag and stress on the tracheostomy wound. These designs disclosed herein can improve quality of patient care by reducing the pain and discomfort associated with aggressive dressing changes, can reduce the formation of pressure ulcers.

FIG. 1 shows a patient following a tracheostomy procedure with a traditional faceplate attached to the neck of the patient. As can be seen, the faceplate lies flat against the patient's neck. The faceplate is shown with a port disposed at each end, which is designed to receive and hold trach straps or ties to secure the faceplate to the patient. However, as shown in the FIG. 1 customary configuration, the faceplate is anchored to the patient via sutures that pass through and occupy the trach strap port. As such, in this configuration, the trach strap port cannot be used for its intended function.

Figure 2A:
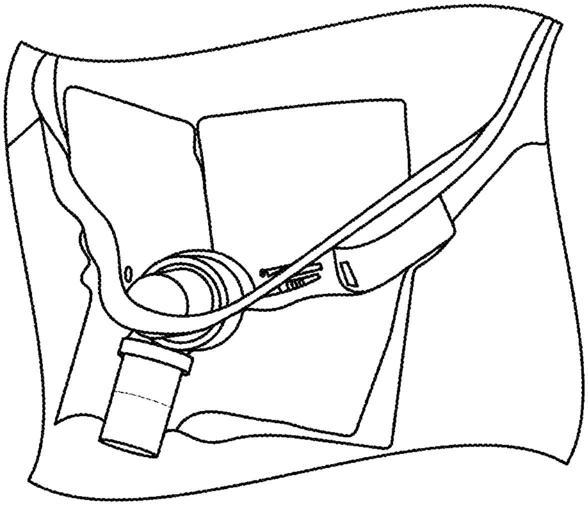
FIG. 2A shows a customary tracheostomy faceplate in use with gauze surrounding the stoma as a wound dressing material. The gauze are pinched between the skin of the patient and the faceplate.

FIG. 2A shows another traditional face plate in use. Once again, the faceplate lies flush with the patient's neck across the entire longitudinal length of the faceplate. The faceplate in the FIG. 2A configuration is attached to the patient via trach straps that extend behind the patient's neck and connect at either end of the faceplate, preventing the use of sutures as an additional anchor. Also, in the FIG. 2A arrangement, gauze have been forced between the faceplate and the neck of the patient as a wound dressing around the stoma. As can be seen, in order to remove or replace the gauze when using a traditional faceplate, the faceplate must be entirely removed or the gauze must be removed sliding the wound dressing across the stoma, which can be painful for the patient and cause further injury.

Figure 2B:
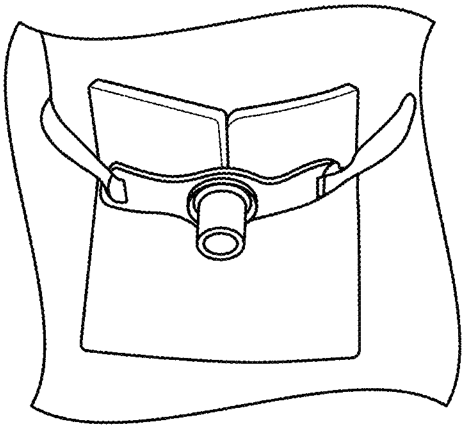
FIG. 2B shows a customary tracheostomy faceplate in use with padding surrounding the soma as a wound dressing material. The padding is pinched between the skin of the patient and the faceplate.

The FIG. 2B configuration is similar to that of FIG. 2A but with padding as the wound dressing material. As can be seen, the configuration of FIG. 2B suffers from the same defects as described above with reference to FIG. 2A.

Figure 3A:
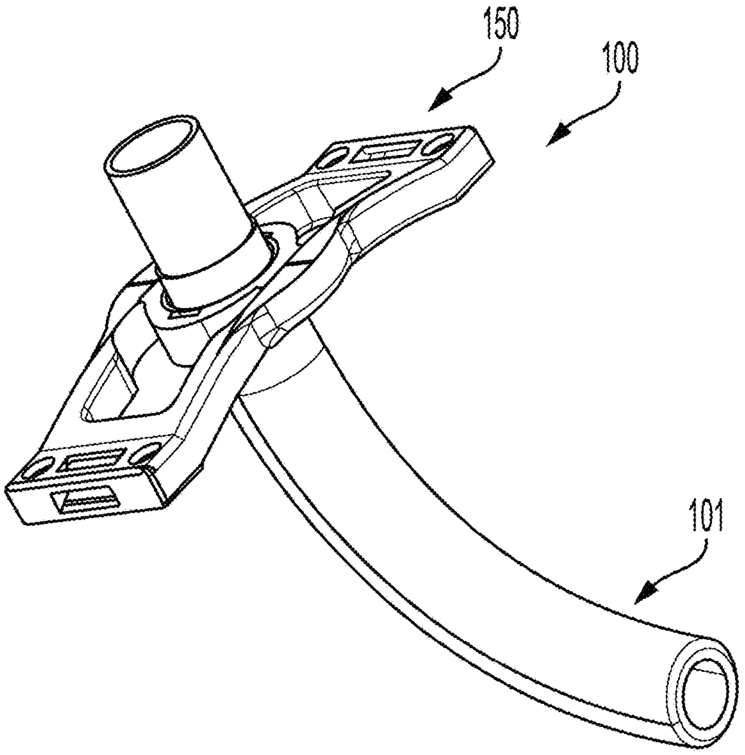
FIG. 3A provides a perspective view of a tracheostomy accessory in accordance with one embodiment of the present invention. The accessory is shown as a faceplate disposed around the outer tracheostomy cannula.

FIG. 3A shows a tracheostomy system or kit 100 with an improved faceplate 150 in accordance with one embodiment of the present invention. The faceplate 150 is shown secured onto an outer tracheostomy cannula 101. In the FIG. 3A embodiment and as clearly shown in FIG. 3B, the faceplate 150 comprises a minimal impact, dual access tracheostomy faceplate.

Figure 3B:
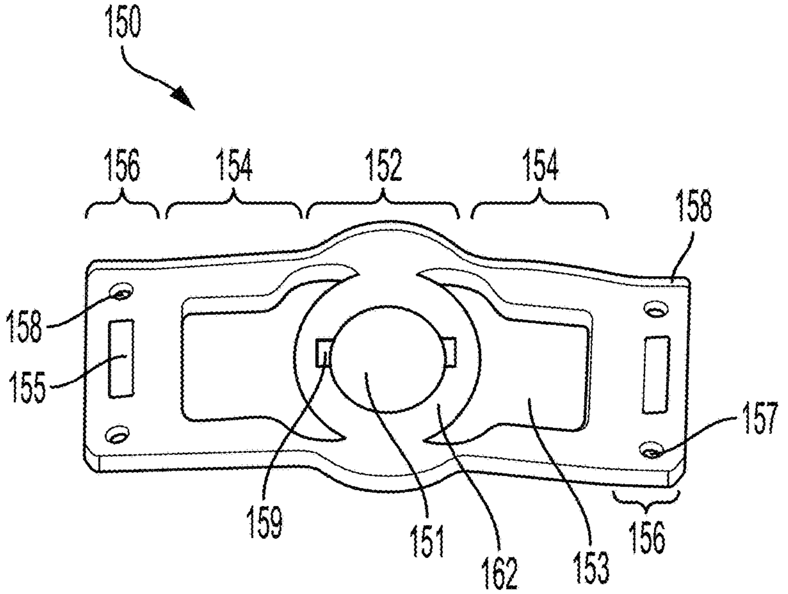
FIG. 3B shows a top view of a tracheostomy faceplate in accordance with one embodiment of the present invention.

The faceplate 150 of FIG. 3B comprises two end sections 156, two linking sections 154, and a central portion 156, which are interconnected such that the faceplate 150 comprises a single, integral unit. In alternate embodiments, any one or more of the central portion, linking sections, and end sections can be detachable. The central portion 152 comprises a cannula holder 162 with a passthrough, hole, or channel 151 extending therethrough that defines as a cannula receiving portion 151 configured to receive and hold the tracheostomy cannula 101 therein. The faceplate 150 of FIG. 3B further includes two passthroughs, holes, or channels 153 that extend through at least a portion of the linking sections 154 and define stomal viewports 153 or stoma viewing windows 153. The stomal viewports 153 are configured to permit a clear view of the stoma of a patient when the faceplate 150 is in use. As more particularly described in embodiments below, the stomal viewports 153 can also serve as stomal access points ease patient stress and discomfort when changing wound dressing material.

The faceplate 150 of the FIG. 3B embodiment further comprises openings and a channel 155 that serve as a tracheostomy tie channel 155 through which a tracheostomy tie or strap can be passed and used to secure the faceplate 150 to the neck of the patient. The faceplate further comprises at least one suture opening 157 through which sutures can be passed and used to anchor the faceplate 150 to the neck of the patient. As shown in the present embodiment, the faceplate 150 can comprise a suture opening 157 at each corner of the footplates 158. In alternate embodiments, the faceplate 150 comprises two suture openings 157. The faceplate 150 can comprise up to 10 suture openings 157. In certain embodiments, the faceplate 150 comprises one, two, three, four, five, six, seven, eight, nine, or ten suture openings 157

Each of the end sections 156 of the FIG. 3B faceplate 150 comprise a footplate 158 that extends laterally from the linking sections 154 is configured to provide support to the faceplate 150 when on the neck of a patient. In embodiments, the footplates 158 represent the only points of direct contact between the faceplate 150 and the patient.

The FIG. 3B embodiment, further comprises a notch 159 in the top surface of the cannula holder 162 that serves as a swivel adapter 159. In embodiments, the swivel adapter 159 allows for securing of the outer cannula 101 within the cannula receiving portion 162 of the faceplate 150. This swivel function prevents the cannula 101 from rotating within the cannula receiving portion 162 of the footplate 150 and allows for micro-adjustments of the tracheostomy cannula 101 and footplate 150 as a unit 100 with patient movement and helps minimize friction and stress ulcers.

Figure 3C:
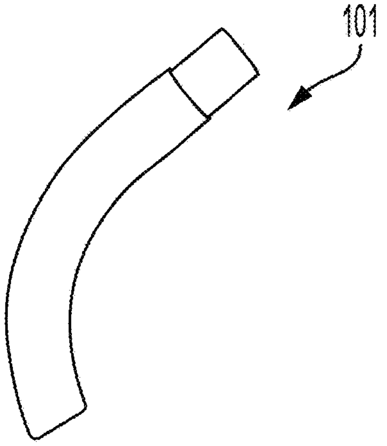
FIG. 3C shows an exemplary outer tracheostomy cannula, for use with the presently disclosed tracheostomy faceplate.

FIG. 3C provides an exemplary tracheostomy cannula that that can be provided with the faceplate 150 of FIG. 3B or obtained separately therefrom.

Figure 4A:
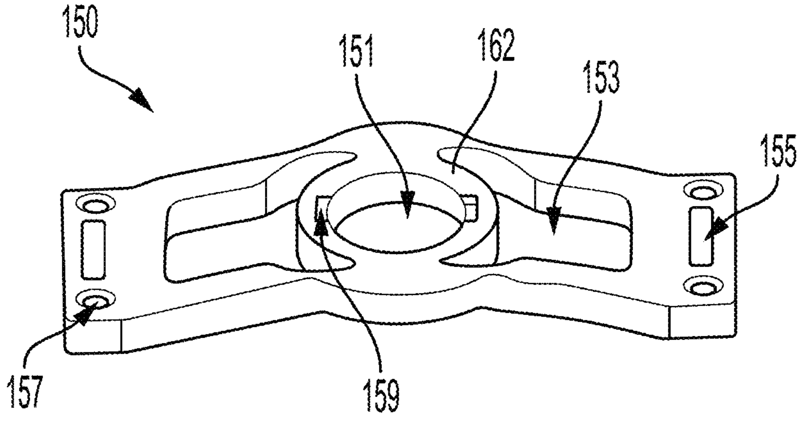
FIG. 4A provides a top perspective view of the tracheostomy face plate under one embodiment.
Figure 4B:
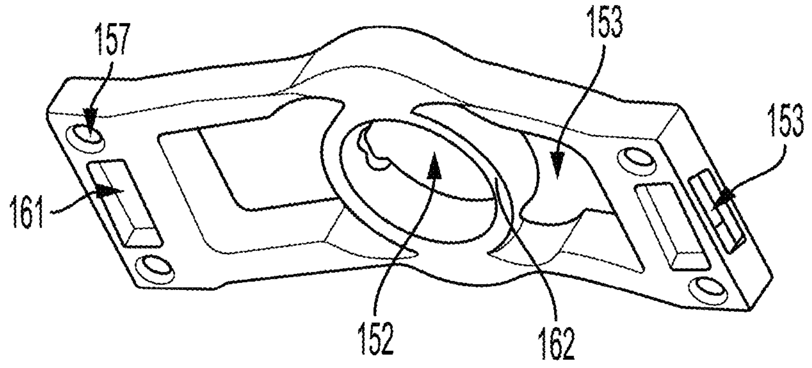
FIG. 4B provides a bottom perspective view of the tracheostomy faceplate of FIG. 4A.

FIGS. 4A and 4B provide a top perspective view and a bottom perspective view, respectively, of a faceplate 150 in accordance with one embodiment. As can be seen, the central portion can comprise a widened section, which can be configured to provide additional support to a cannula when placed within the cannula receiving portion 151 of the faceplate 150.

As shown in FIG. 4B, the undersurface of each footplate 158 can comprise a cushion inset 161 that is configured to receive and hold a cushion (seen at 160 of FIGS. 5B & 5C and discussed in more detail below.) In addition, FIG. 4B provides a clear view of the tracheostomy tie channel 155, which can be seen extending from the front surface to the top surface of the footplate 158.

Figure 4C:
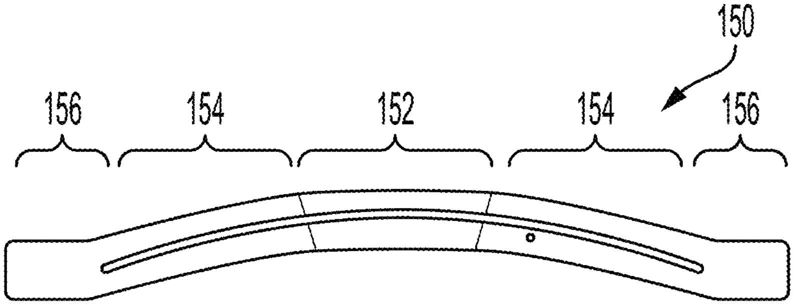
FIG. 4C provides a side view of the faceplate of FIG. 4A.

As clearly shown in the side view of FIG. 4C, the center section 152 is elevated as compared to the linking sections 154 and the end sections 156 to create a creep space between the faceplate 150 and the patient. FIG. 4C also reveals that linking sections 154 comprise a curvature that extends upward from the end sections 156 until reaching its highest point at the central portion 152 to form a substantially arched faceplate 150. FIG. 4C provides a side view of the embodiment of FIGS. 4A and 4B. This view more clearly shows the footplates 158 extending laterally from the linking sections 154 to provide support for the footplate 150 and cannula 101 while in use.

Figure 5A:
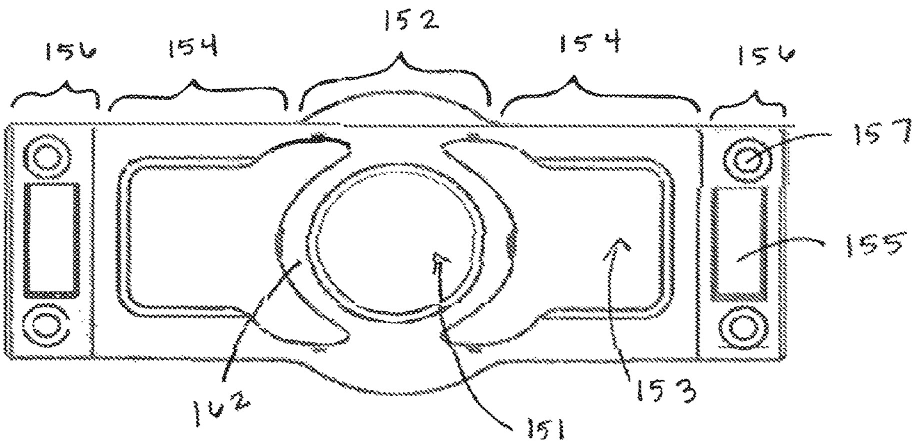
FIG. 5A shows a schematic top view of a faceplate under one embodiment.

FIG. 5A provides a schematic top view of a faceplate 150 under one embodiment. The features of FIG. 5A are discussed in detail above with reference to FIG. 3A.

Figure 5B:
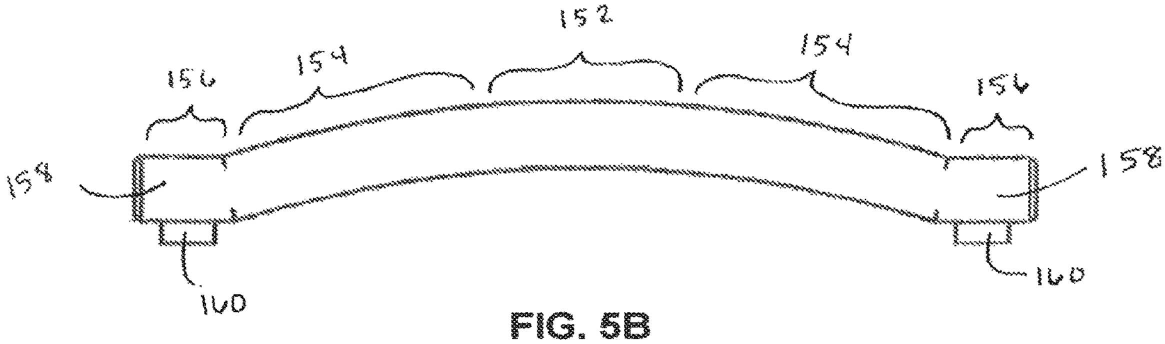
FIG. 5B provides a side view of the FIG. 5A schematic.
Figure 5C:
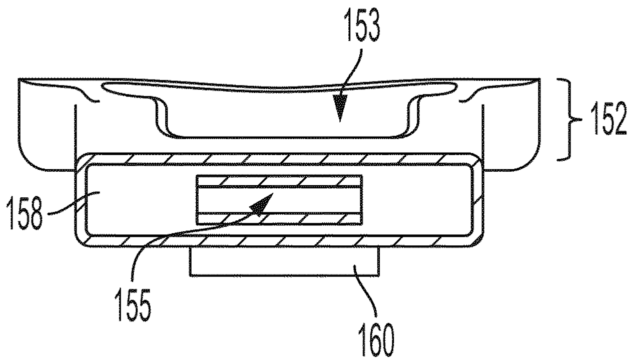
FIG. 5C shows a front view of the FIG. 5A schematic.

As shown in FIGS. 5B & 5C, each footplate 158 can comprise a cushion 160 attached to its undersurface. In such embodiments, the cushion 160 provides padding and additional patient comfort and is configured to reduce the formation of pressure ulcers and minimize trauma to the skin of the patient. Alternate embodiments can comprise a sleeve (seen at 458 of FIG. 14) or other means of covering the ends of the footplate 158, which can be used in combination with the cushions 160 or alone to reduce patient discomfort, the formation of pressure ulcers, irritation, or other traumatic skin injury. FIG. 5C provides a front view of the faceplate 150 of FIG. 5A. One opening of the tracheostomy tie channel 155 can be seen extending through the front face of the footplate 158, which terminates in an opening 155 of the top face of the footplate 158 (seen at 155 of FIG. 5A).

Figure 6A:
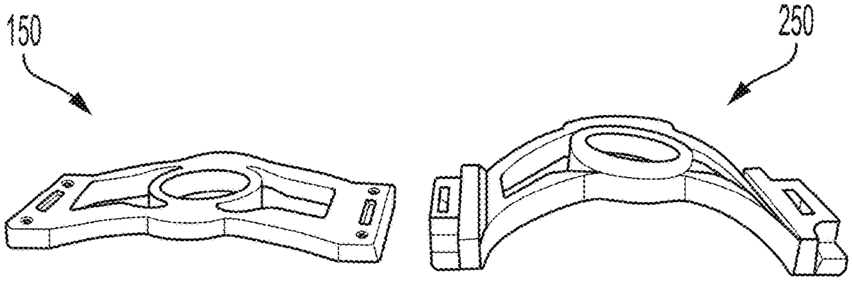
FIG. 6A provides a side view of two different exemplary embodiments of the present invention. A short embodiment is shown on the left and a tall embodiment is shown in the right.

FIG. 6A provides a photographic side perspective view showing how the height can vary between different embodiments of the present invention. A short embodiment 150 is shown on the left of the figure, and a tall embodiment 250 can be seen at the right of figure. The tall embodiment 250 comprises increased creep space underneath the faceplate as compared to the short embodiment 150. The increased creep space can provide additional room for a caretaker to access the stoma or change wound dressing material.

Figure 6B:
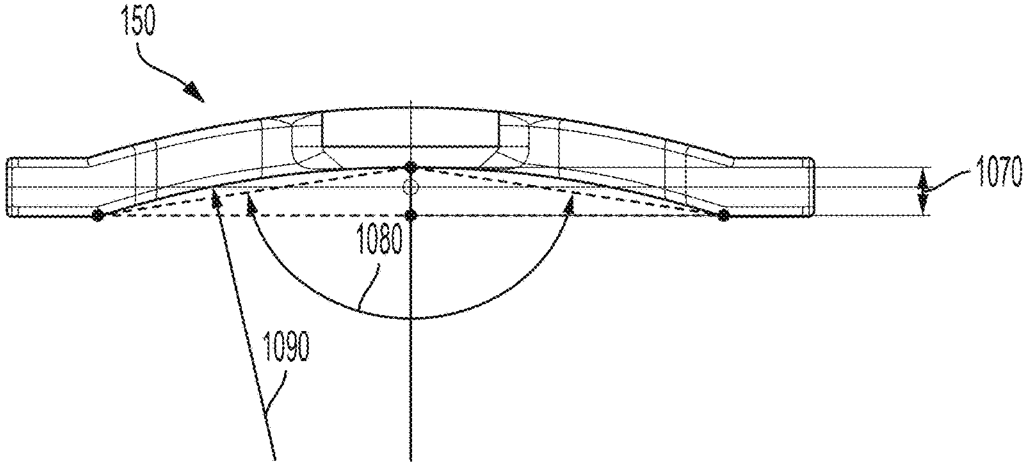
FIG. 6B shows a schematic side view of the short embodiment (left) of FIG. 6A. Exemplary dimension of the embodiment are shown.

FIG. 6B provides exemplary dimensions for a short faceplate embodiment. As can be seen, the short embodiment can comprise a creep space height 1070 of about 5 mm. The radius of curvature 1090 can be about 90 degrees, and the mean angle of curvature 1080 can be about 160 degrees.

Figure 6C:
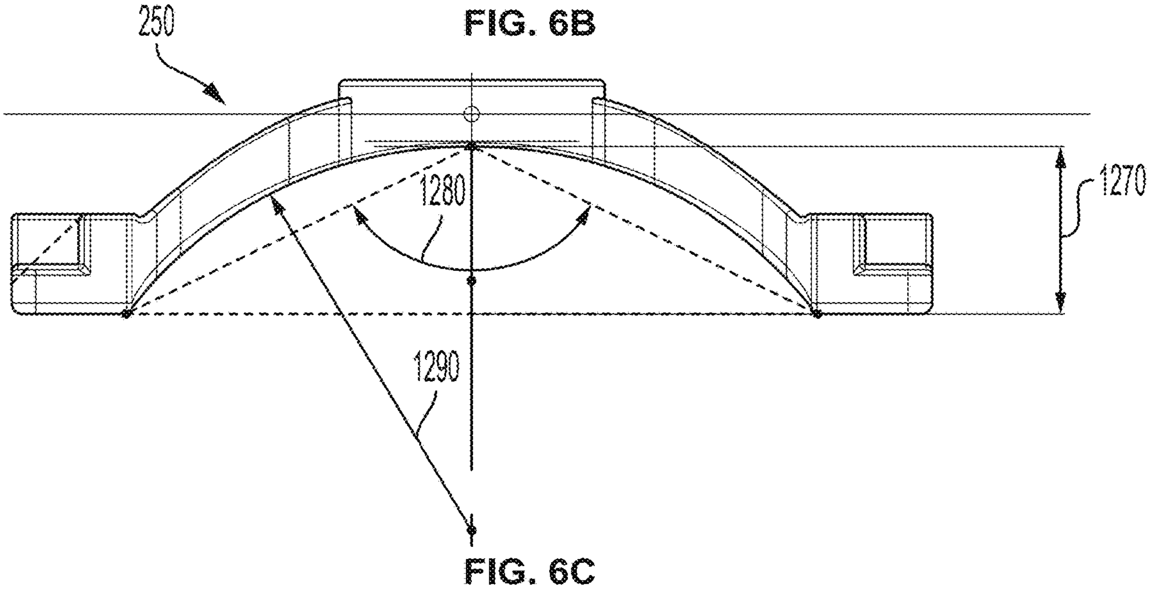
FIG. 6C shows a schematic side view of the tall embodiment (right) of FIG. 6A. Exemplary dimension of the embodiment are shown.

FIG. 6C provides an exemplary dimension for a tall faceplate embodiment. As can be seen, the tall embodiment can comprise a creep space height 1270 of about 15 mm, a radius of curvature 1290 of about 35 degrees and a mean angle of curvature 1280 of about 125 degrees.

In embodiments, the height of the faceplate can be as large as about 30 mm. The height of the faceplate can be as small as 1 mm. The faceplate can comprise a height any height ranging from about 3 mm to about 25 mm. In embodiments, the faceplate comprises a height of about 4 mm, about 5 mm, about 5 mm, about 7 mm, about 8 mm, about 9 mm, about 10 mm, about 11 mm, about 12 mm, about 13 mm, about 14 mm, about 15 mm, about 15 mm, bout 17 mm, about 18 mm, about 19 mm, or about 20 mm.

In exemplary embodiments, the radius of curvature 1090, 1290 can be as high as about 100 degrees. The radius of curvature 1090, 1290 can be as low as about 15 degrees. In embodiments, the radius of curvature 1090, 1290 ranges from about 20 degrees to about 100 degrees. The radius of curvature 1090, 1290 can be about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, about 90 degrees, about 95 degrees, or about 100 degrees In various exemplary embodiments, the mean angle of curvature 1080, 1280 can be as high as about 170 degrees. The mean angle of curvature 1080, 1280 can be as low as about 100 degrees. In embodiments, the mean angle of curvature 1080, 1280 ranges from about 110 degrees to about 170 degrees. The mean angle of curvature 1080, 1280 can be about 120 degrees, about 130 degrees, about 140 degrees, about 150 degrees, about 160 degrees, or about 170 degrees.

Figure 7A:
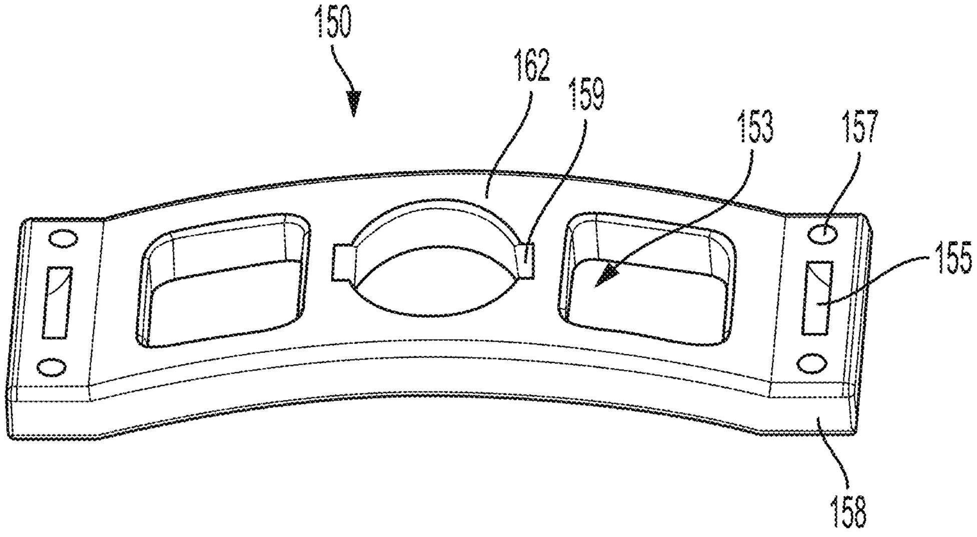
FIG. 7A provides a top perspective view of an exemplary embodiment of a short faceplate. The embodiment is shown with generally square stomal view ports. An optional widening of the central portion can be seen in the blue lines and an alternate view port shape is shown in the green lines.
Figure 7B:
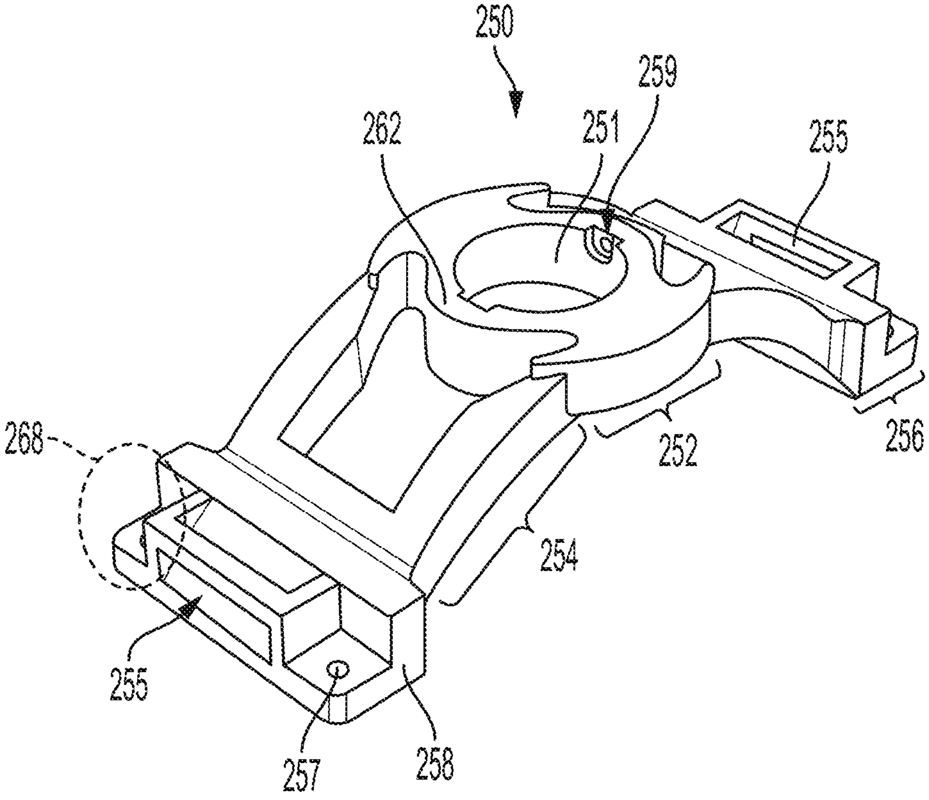
FIG. 7B shows a top perspective view of an exemplary embodiment of a tall faceplate.

FIG. 7A shows a faceplate 150 under one embodiment with a substantially square-shaped stoma viewport 153. As shown in the lined overlay, alternate stoma viewports FIG. 7B is a top perspective view of a tall faceplate 250 under one embodiment. The faceplate 250 of FIG. 7B comprises two end sections 256, two linking sections 254, and a central portion 256. The central portion 252 comprises a cannula holder 262 with a passthrough, hole, or channel 251 extending therethrough that defines as a cannula receiving portion 251 configured to receive and hold a tracheostomy cannula (seen at 201 of FIGS. 8A & 8B) therein. The faceplate 250 of FIG. 7B further includes two passthroughs, holes, or channels 253 that extend through at least a portion of the linking sections 254 and define stomal viewports 253 or stoma viewports 253.

Each of the end sections 256 of the FIG. 7B faceplate 250 comprise a footplate 258 that extends laterally from the linking sections 254 is configured to provide support to the faceplate 250 when on the neck of a patient.

The faceplate 250 of the FIG. 7B embodiment further comprises openings and a channel 255 that serve as a tracheostomy tie channel 255 through which a tracheostomy tie or strap can be passed and used to secure the faceplate 250 to the neck of the patient. The faceplate further comprises at least one suture opening 257 through which sutures can be passed and used to anchor the faceplate 250 to the neck of the patient. As shown in the present embodiment, the faceplate 250 can comprise a suture opening 257 at each corner of the footplates 258. Each corner of the footplate 258 can comprise a recessed portion 268 that permits the suture openings 257 to lie against the skin of the patient. The recessed portion 268 further creates a stepped tracheostomy tie channel 255 that permits the tracheostomy strap or tie to pass through the front of the footplate 258 and avoid contacting the skin of the patient.

The FIG. 7B embodiment, further comprises a notch 259 in the top surface of the cannula holder 262 that serves as a swivel adapter 259.

Figure 8A:
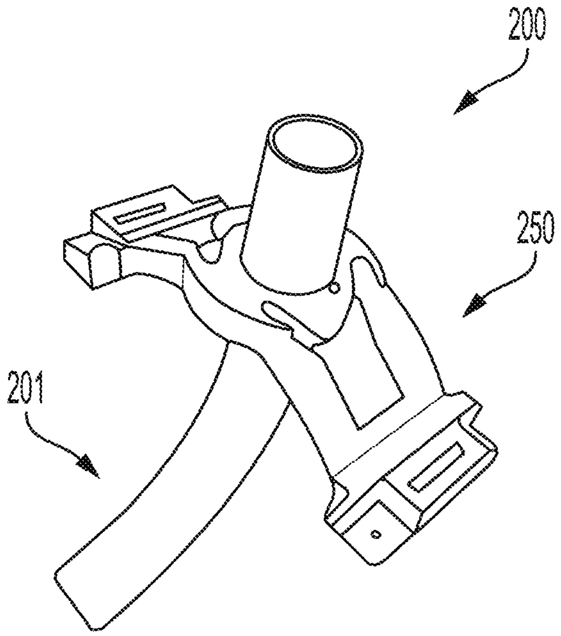
FIG. 8A provides a top perspective photographic view of the FIG. 7B embodiment in place around an outer cannula.
Figure 8B:
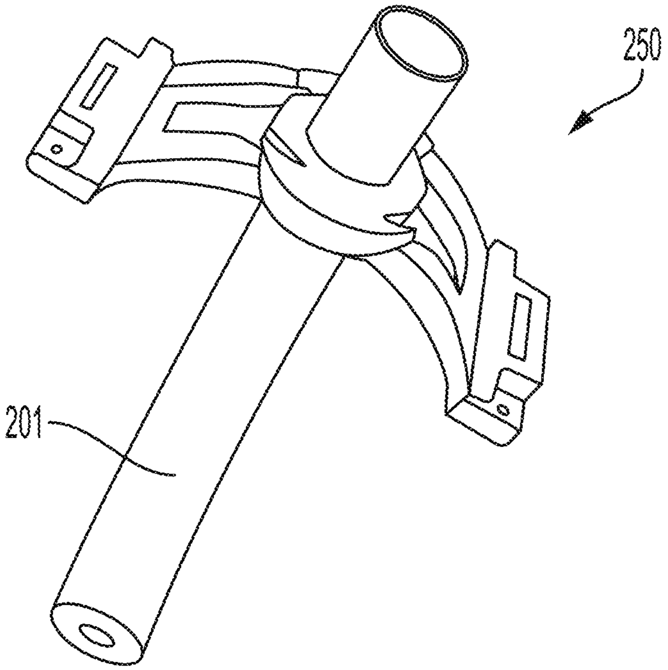
FIG. 8B provides an alternate top perspective photographic view of the FIG. 7B embodiment in place around an outer cannula.

FIGS. 8A and 8B are photographic perspective views of a tracheostomy system or kit 200 with a faceplate 250 in accordance with a tall embodiment of the present invention. The faceplate 250 is shown secured onto an outer tracheostomy cannula 201.

Figure 9A:
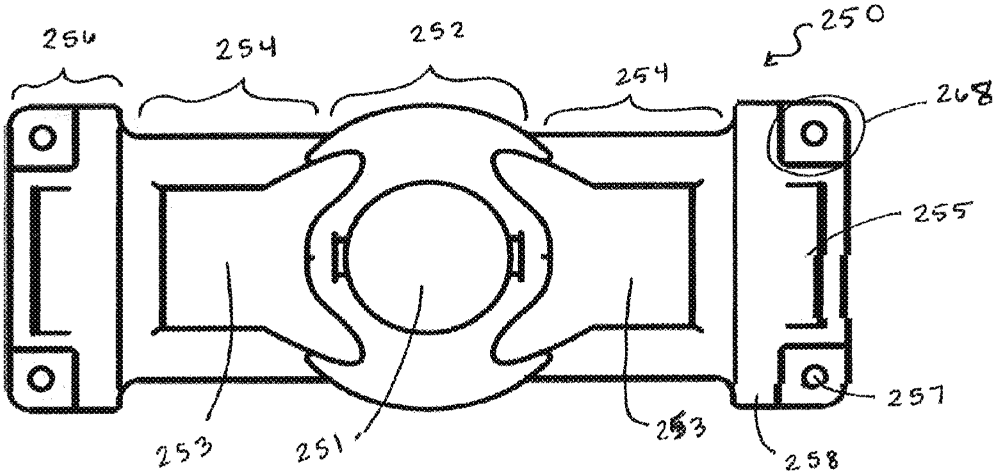
FIG. 9A is a top schematic view of a tall faceplate under one embodiment.

FIG. 9A is a top schematic view in accordance with one embodiment of a tall faceplate 250. The faceplate 250 is shown with a central section 252, two linking sections 254, and two end sections 256. Each end section comprises a footplate . . . .

FIGS. 8A, 8B, and 8C provide a top perspective view, a bottom perspective view, and a side perspective view, respectively, in accordance with one embodiment of a tall faceplate 250.

The faceplate 250 comprises a central portion 252, two linking sections 254, and two end sections 256. As can be seen, the end sections 256 each comprise a footplate 258. The recessed portion 268 of the footplate 258 can be seen at every corner of the footplate 256 with a suture opening 257 therein.

Figure 9B:
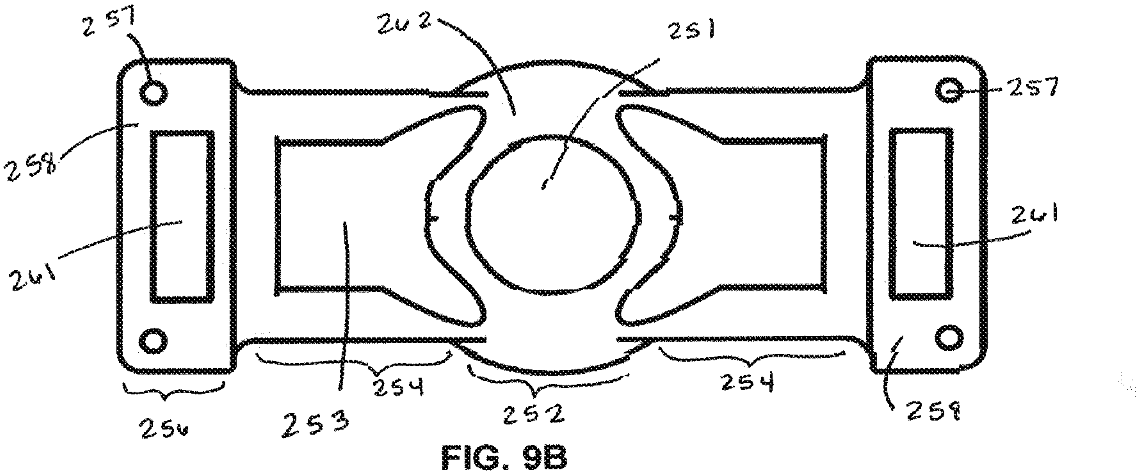
FIG. 9B shows a bottom schematic view of the FIG. 9A embodiment.

As discussed above with reference to the short embodiment of FIG. 4B, FIG. 9B, reveals that the undersurface of the footplate 258 can comprise a channel, notch, or inset that serves as a cushion inset 261 configured to receive and hold a cushion (seen more clearly at 160, 260 of FIGS. 4B, 5B, 5C, & 10B).

Figure 10A:
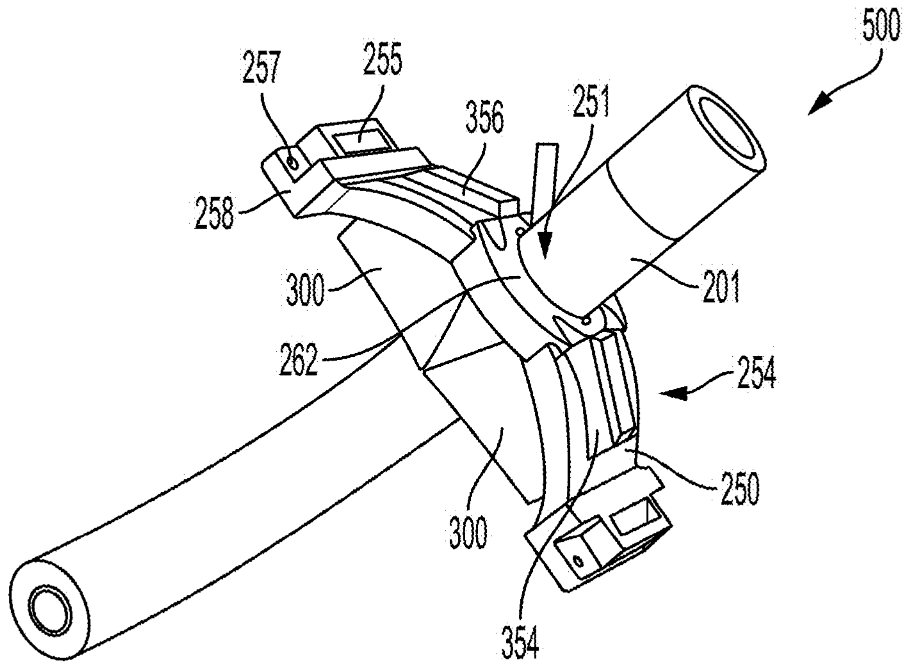
FIG. 10A shows a top perspective view of a tall faceplate secured to an outer tracheostomy cannula under an embodiment that further includes wound dressing material. The wound dressing material can be seen residing in the space underneath the faceplate.

FIG. 10A provides a top perspective view of a tall faceplate 250 secured to an outer tracheostomy cannula 201 under an embodiment that further includes wound dressing material 300. The wound dressing material can be seen residing in the creep space underneath the faceplate 250. In operation, the bottom of the wound dressing material 300 will rest on the skin of the patient and a portion will encircle the cannula such that the wound dressing material 300 will serve a dressing to soak any tracheal secretions or blood coming from the stoma. As shown in the FIG. 10 embodiment, the wound dressing material 300 can comprise a sponge 300. However, in alternative embodiments, the wound material comprises any material or substance that is capable of absorbing drainage or exudate from a wound. The material can include, but is not limited to gauze, foam, packing strips, sponges, or any open-cell, absorbent, or porous material.

A top portion 354 of the wound dressing material 300 is shown extending at least partially into the stoma viewport 253 of the faceplate 250. The wound dressing material 300 can further comprise an extension 356 that extends beyond the top surface of the faceplate 250. This extension can serve as a gripping point or handle 356 to assist with removal of the wound dressing material 300 from the space between the faceplate 250 and the skin of the patient. In certain embodiments, the top of the wound dressing material 300 or the handle 356 can be leveled with or rise above the top surface of the faceplate 250.

Figure 10B:
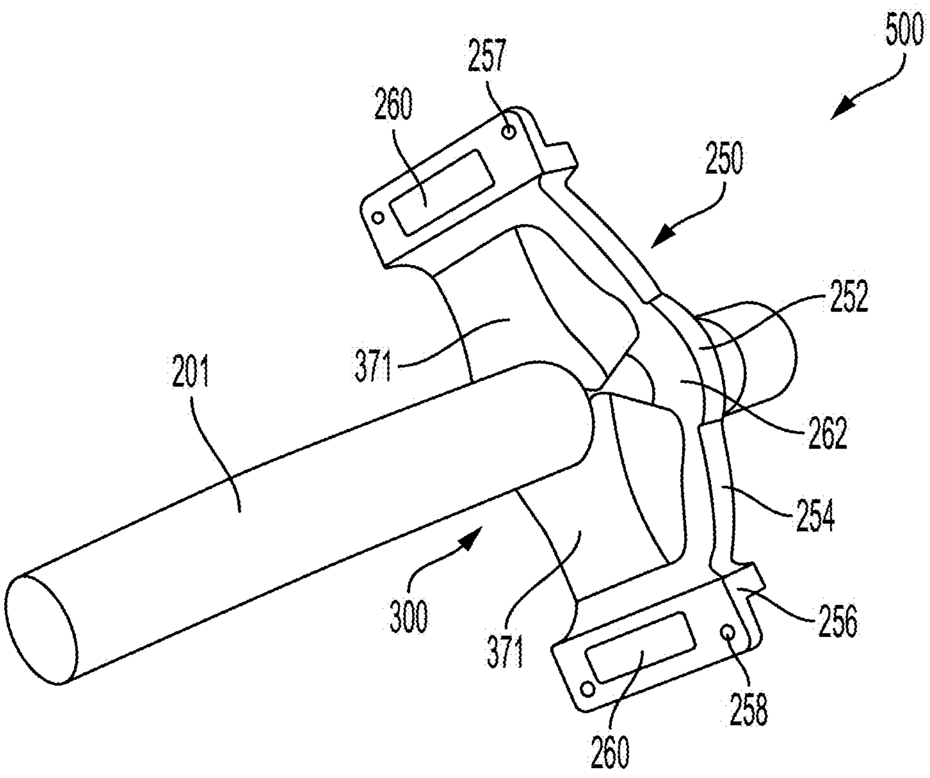
FIG. 10B provides a bottom perspective view of the FIG. 10A embodiment.

FIG. 10B provides a bottom perspective view of the FIG. 10A embodiment. The bottom surface 371 of the wound dressing material 300 can be seen. In operation, it is understood that the bottom surface 371 of the wound dressing material 300 is in direct contact with the skin of the patient. It is further noted that, during operation of the faceplate 250, the wound dressing material 300 can provide additional stability for the cannula 201 and faceplate 250 when disposed within the creep space beneath the faceplate 250.

In certain embodiments, at least a portion of the top surface of the wound dressing material 300, a bottom surface 371 of the wound packing material 300, or a combination thereof can be coated with an adhesive material that serves to further secure the wound packing material 300 to the patient, the faceplate 250 or both.

Figure 10C:
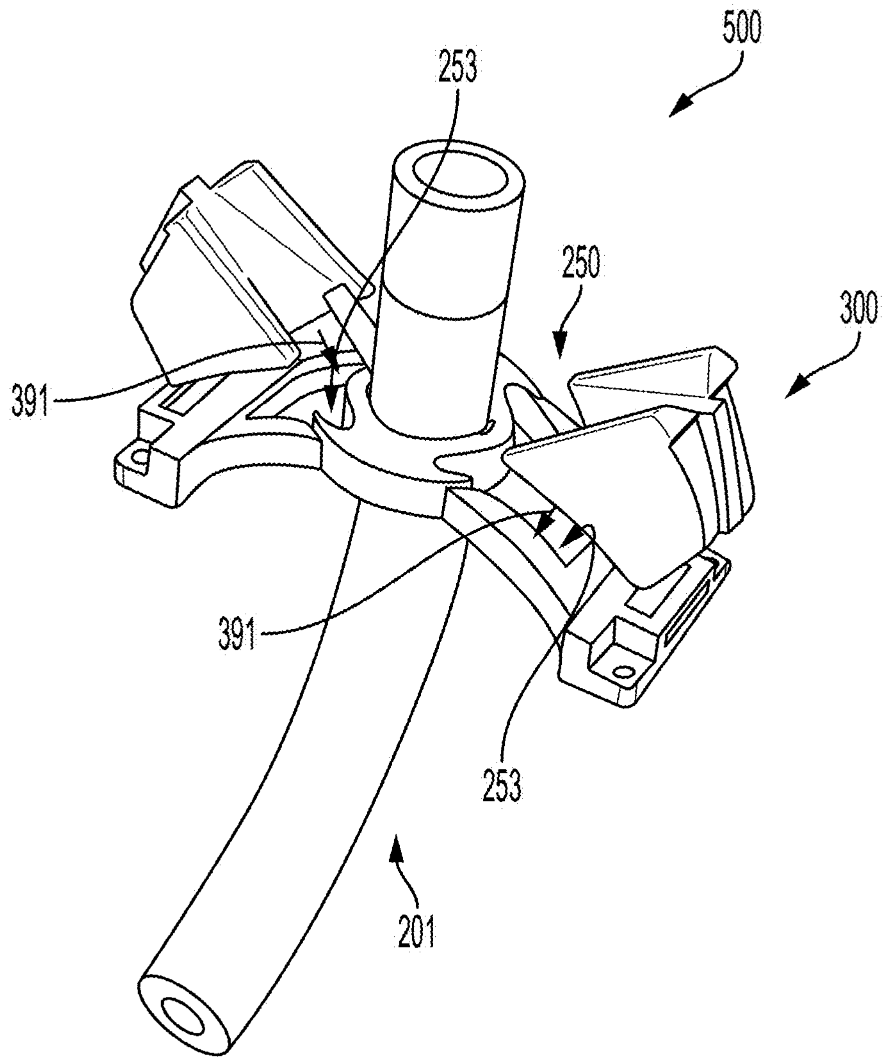
FIG. 10C shows an alternate top perspective view of the FIG. 10A embodiment. The wound dressing material can be seen exploded above the stomal windows of the faceplate in preparation for insertion therethrough.

FIG. 10C shows an alternate top perspective view of the FIG. 10A embodiment. The wound dressing material 300 can be seen exploded above the stomal windows 253 of the faceplate in preparation for insertion therethrough. As can be seen, when the faceplate 250 resides on the neck of the patient during use the wound dressing material 300 can be readily inserted and removed through the stomal viewports 253. In operation, the wound dressing material 300 can be moved in the direction of arrows 391 to be placed through the stomal windows 253 until the bottom surface of the wound dressing material 300 contacts the skin of the patient and a top portion 354 of the wound dressing material 300 resides within the stoma viewport 253 of the linking section 254.

Figure 11A:
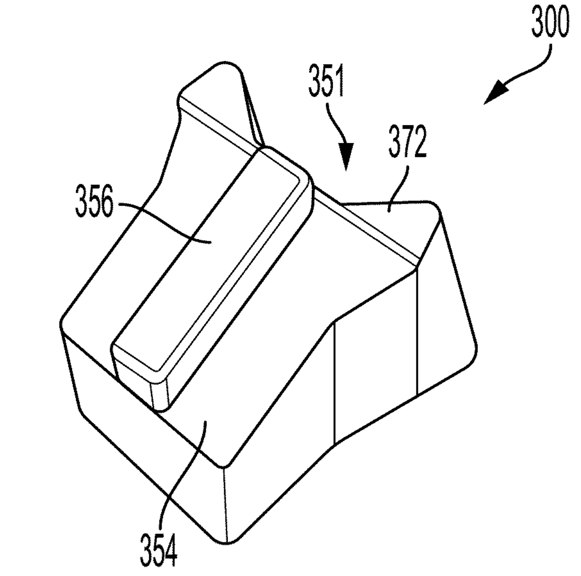
FIG. 11A provides a top, rear perspective view of a sponge that serves as an exemplary wound dressing material in FIGS. 10A-10C.

FIG. 11A provides a top, rear perspective view of a sponge 300 that serves as an exemplary wound dressing material in FIGS. 10A-10C.

Figure 11B:
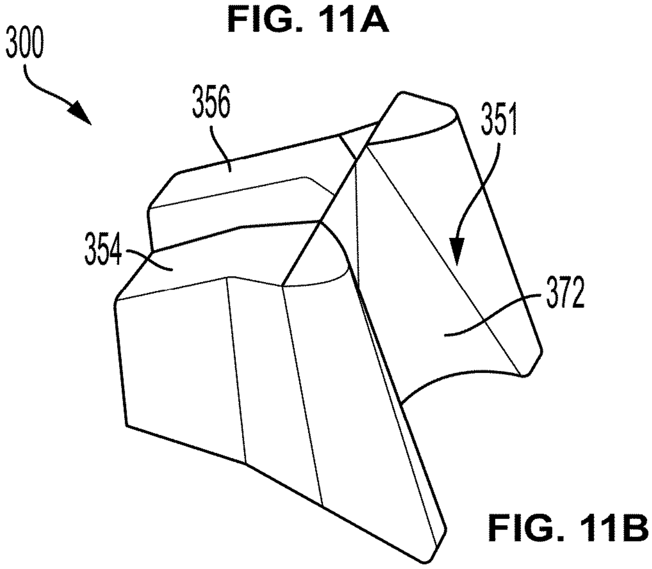
FIG. 11B shows a top, front perspective view of the FIG. 11A sponge.

FIG. 11B shows a top, front perspective view of the FIG. 11A sponge 300.

Figure 11C:
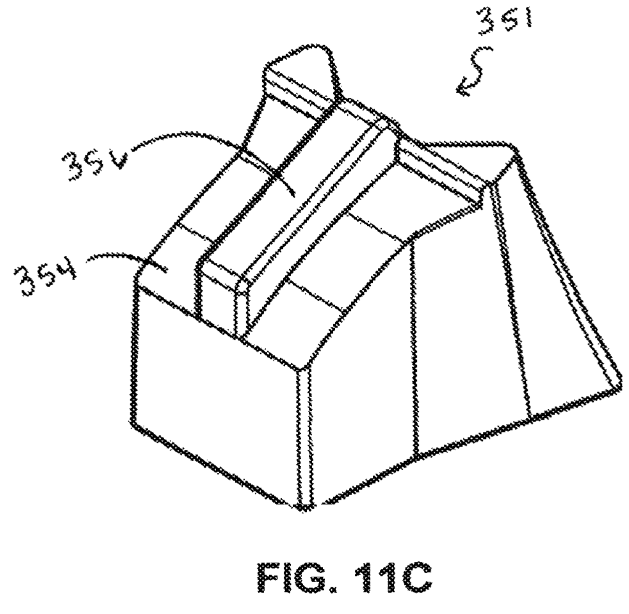
FIG. 11C provides a top, rear perspective view of a schematic of the FIG. 11A sponge.

FIG. 11C provides a top, rear perspective view of a schematic of the FIG. 11A sponge.

Figure 11D:
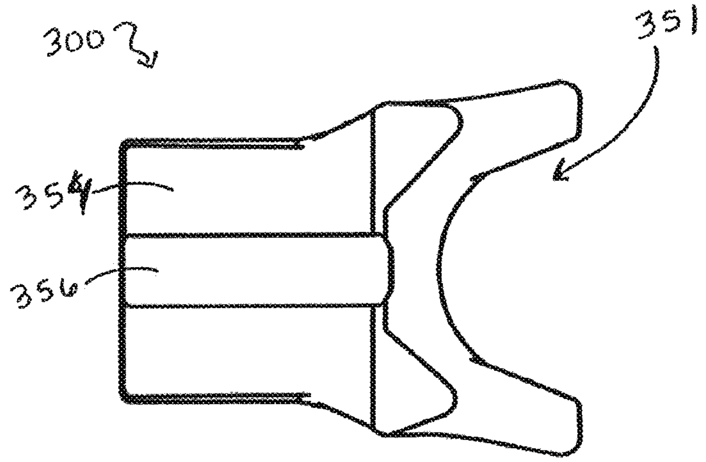
FIG. 11D shows a top view of the FIG. 11C sponge schematic.

FIG. 11D shows a top view of the FIG. 11C sponge 300 schematic.

Figure 11E:
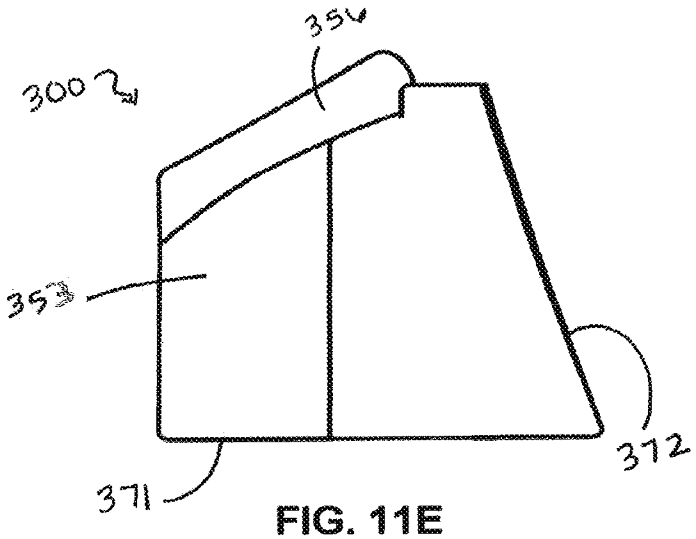
FIG. 11E provides a side view of the FIG. 11C schematic.

FIG. 11E provides a side view of the FIG. 11C schematic.

Figure 11F:
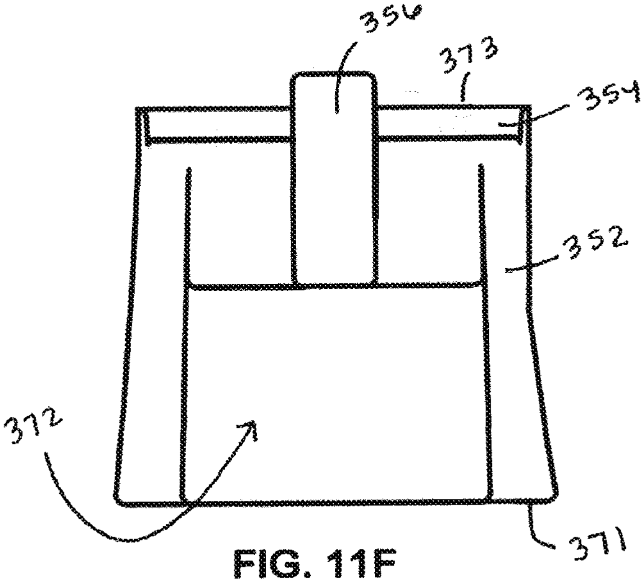
FIG. 11F provides a front view of the FIG. 11C schematic.

FIG. 11F provides a front view of the FIG. 11C schematic.

Figure 11G:
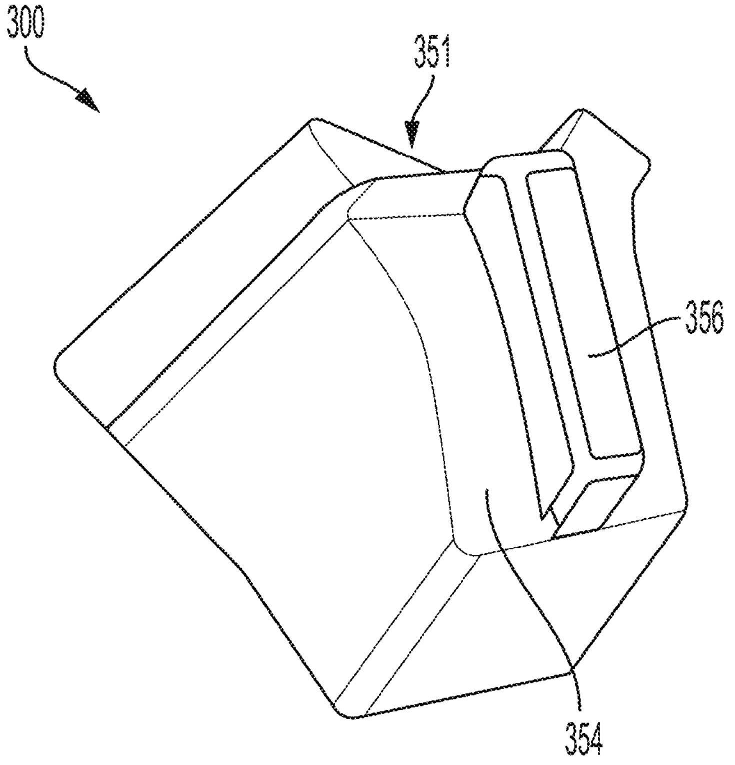
FIG. 11G shows a top perspective view of the FIG. 11A sponge. A handle is clearly visible on the top of this sponge.

FIG. 11G provides an alternative top perspective rear view of the FIG. 11A embodiment that accentuates the presence of an optional extension or handle 356 on the top of the sponge 300.

The sponge 300 comprises a top surface 354, a front surface 372, and a bottom surface 371. As discussed above with reference to FIG. 10A, the sponge 300 can further include an extension or handle 356 that can be useful in removing the sponge 300 such as during a wound dressing change. The extension or handle 356 can facilitate insertion and removal of the sponge into the view port.

The sponge 300 can comprise a cannula receiving portion 351 along the front surface 372 that is configured to extend at least partially around the curvature of the cannula. In embodiments, the cannula receiving portion 351 of the sponge 300 comprises a structure that is complementary to the shape of the cannula 201.

Figure 12A:
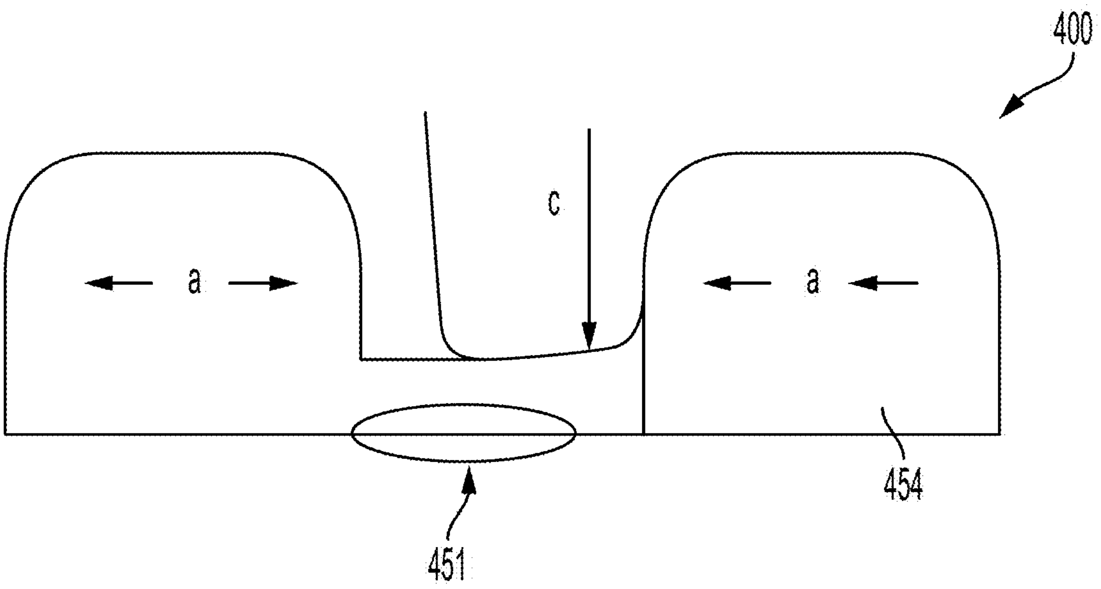
FIG. 12A is a sketch showing the side view of a sponge design as an alternate embodiment.

FIG. 12A is a sketch showing the side view of a sponge design as an alternate embodiment.

Figure 12B:
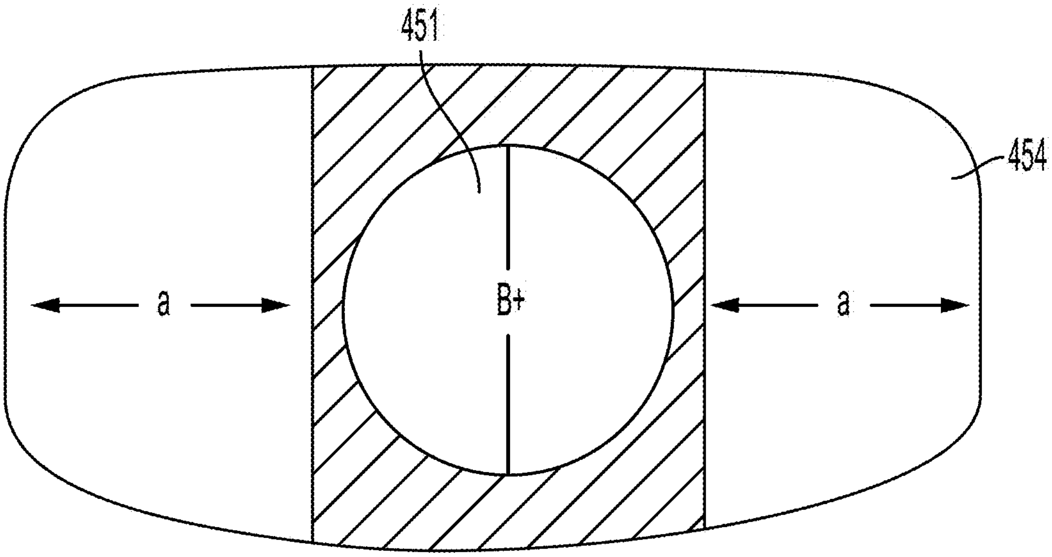
FIG. 12B is a top view of the FIG. 12A sponge.

FIG. 12B is a top view of the FIG. 12A sponge.

Figure 12C:
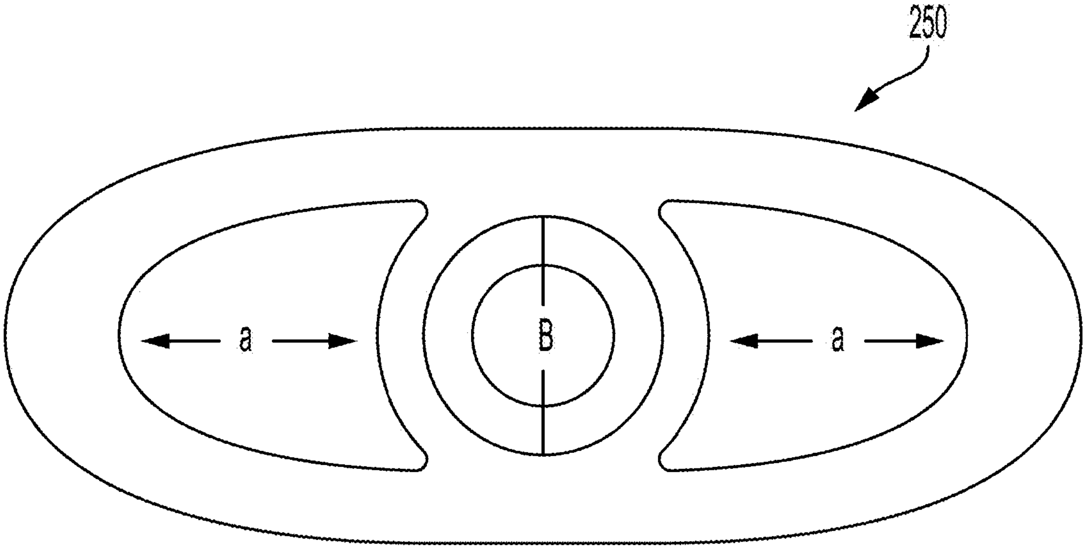
FIG. 12C provides a top view of a faceplate for use in association with the sponge of FIG. 12A.

FIG. 12C provides a top view of a faceplate for use in association with the sponge of FIG. 12A.

Figure 12D:
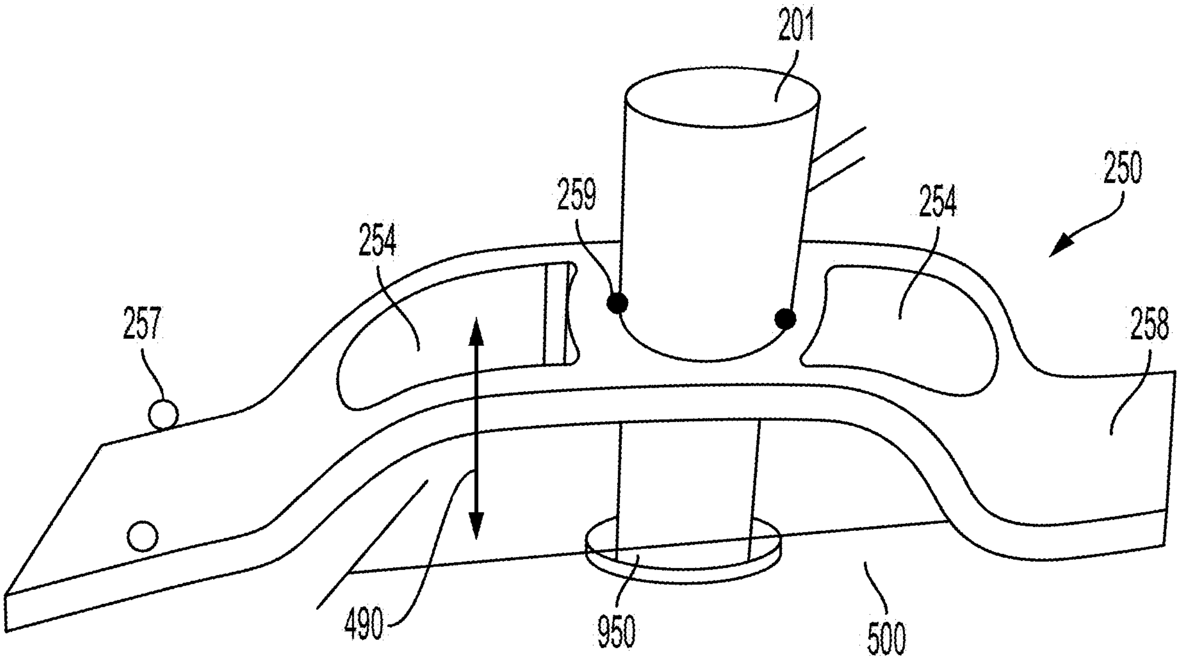
FIG. 12D provides a top side perspective view of the FIG. 12C face plate lying on the skin of a patient with a tracheostomy cannula extending through the central portion of the faceplate.

FIG. 12D provides a top side perspective view of the FIG. 12C faceplate 250 lying on the skin 900 of a patient with a tracheostomy cannula 201 extending out from the stoma 950 and through the central portion 252 of the faceplate 250. As shown in FIG. 12D, a creep space 490 is formed between the bottom of the faceplate 250 and the skin 500 of the patient. In embodiments, the representative space 490 can be filled with a wound dressing material 300 such as any of the sponges or alternate material disclosed herein.

Figure 13A:
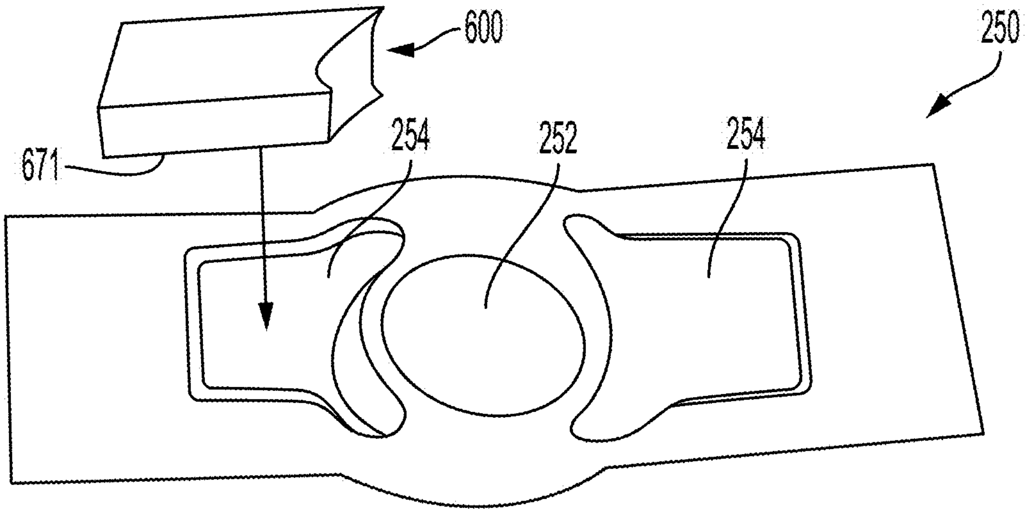
FIG. 13A is a sketch of a sponge and faceplate in accordance with another embodiment of the present invention. A top perspective view of the sponge is provided exploded above a top view of the faceplate.
Figure 13B:
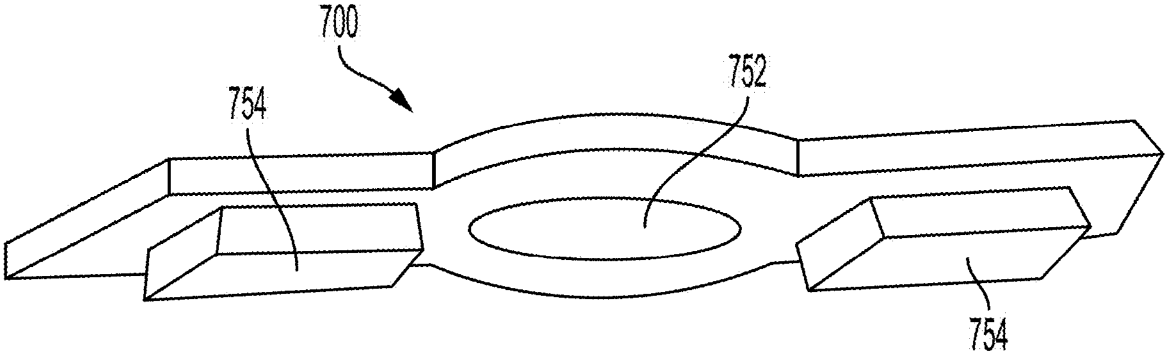
FIG. 13B shows a sketch of a sponge in an alternate embodiment. The sketch shows a bottom perspective view of a single sponge with two protrusions extending downward and a central cannula receiving portion.
Figure 13C:
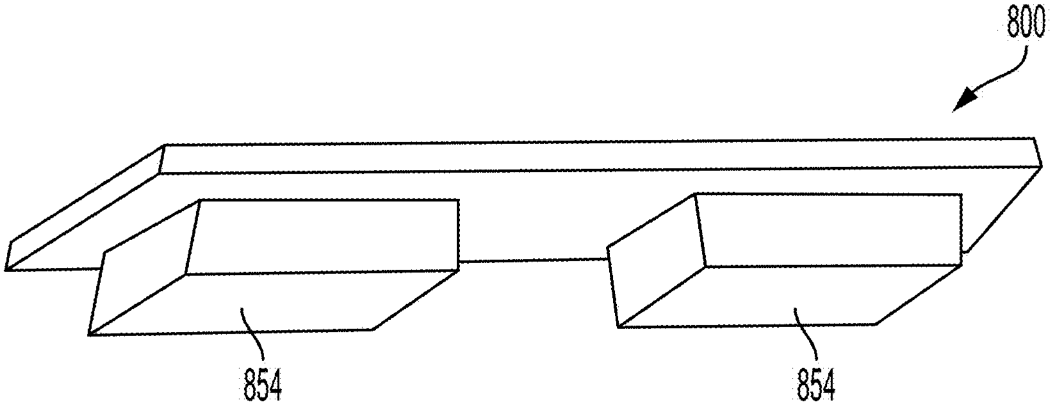
FIG. 13C provides a sketch of a sponge in yet another embodiment. The sketch shows a bottom perspective view of a single sponge with two protrusions extending downward. The pictured embodiment does not comprise a cannula receiving portion.

FIGS. 13A-13C provide various exemplary embodiments of wound dressing material 600, 700, 800 that can be employed in the current invention. FIG. 13A provides a general schematic of the wound dressing material 600 discussed above that can be inserted through the stoma viewports 253 to reside completely between the faceplate 250 and the skin of the patient (as shown in FIGS. 10A-10C). In such embodiments, the sponge 600 can comprise an adhesive material 671 on its bottom surface that is configured to reversibly secure the sponge 600 in place once applied to the skin of a patient.

Figure 14:
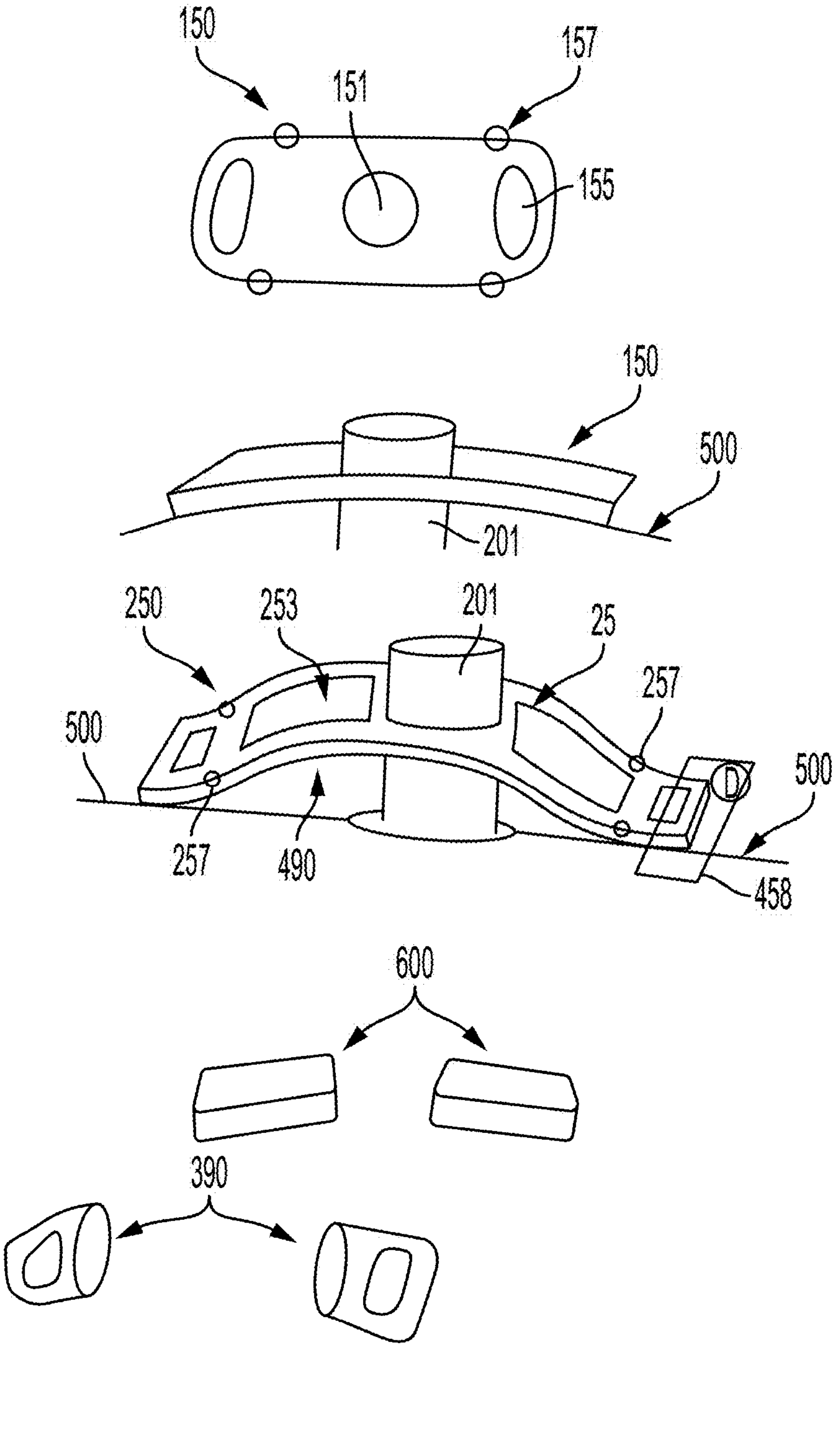
FIG. 14 provides a schematic view that further describes the tracheostomy accessory under multiple embodiments.

FIG. 14 shows schematic views of tracheostomy accessories under multiple embodiments. A top view of one embodiment can been seen at the top of FIG. 14. The second image from the top shows a side view of one embodiment 150 in place around a cannula 201 and resting on the skin of a patient 500. The third image from the top shows a side perspective view of another embodiment 250 holding a cannula 201 in place on a patient 500. A creep space 490 can be seen in the area between the patient 500 and the tracheostomy accessory 250. The bottom images represent exemplary sponges 600, 390 that can be used as wound dressing material.

Figure 15A:
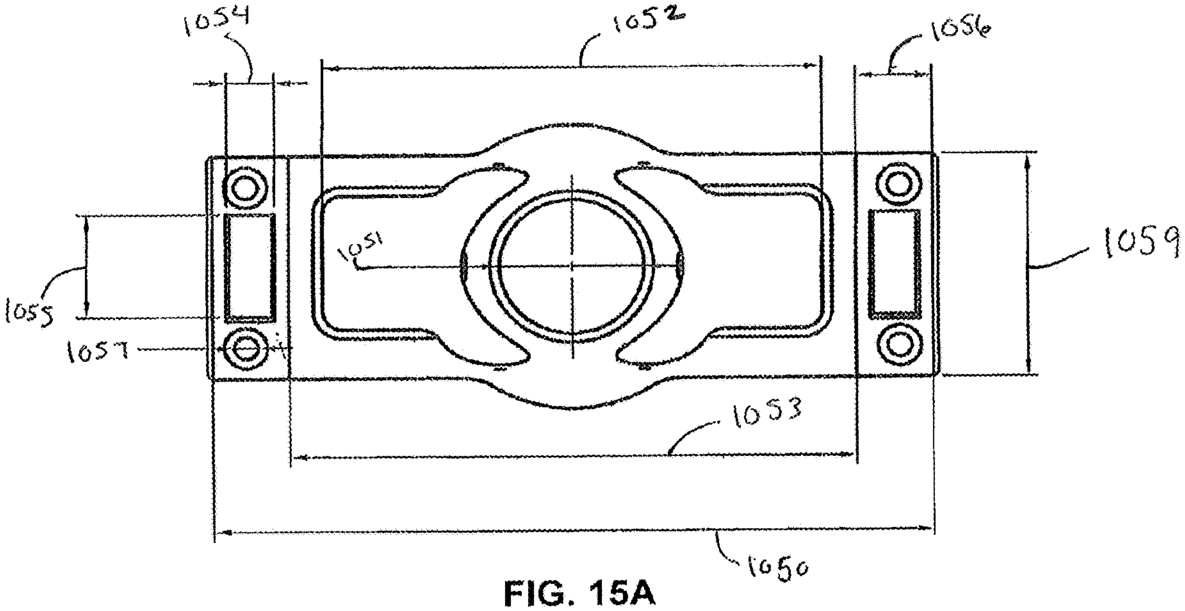
FIG. 15A provides exemplary dimensions of the faceplate of FIG. 5A.

FIG. 15A provides exemplary dimensions of the faceplate of FIG. 5A. The length 1050 of this embodiment can be about 75 mm. In embodiments, the area comprising the two linking sections (seen at 154 of FIG. 5A) and central portion (seen at 152 of FIG. 5A) comprises a length 1053 of about 60 mm. In embodiments, the distance between opposite ends of the two stoma viewports (seen at 153 of FIG. 5A) is about 52 mm. The a cannula receiving portion (seen at 151 of FIG. 5A) can comprise a diameter of about 15 mm. The end section (seen at 156 of FIG. 5A) can comprise a length 1056 of about 8 mm and a width 1059 of about 25 mm. In certain embodiments, the tracheostomy tie channel (seen at 155 of FIG. 5A) comprises a width 1055 of about 11.5 mm, a length 1054 of about 5 mm, or a combination thereof. In one embodiment, at least one suture opening (seen at 157 of FIG. 5A) comprises a diameter of about 2.5 mm.

Figure 15B:
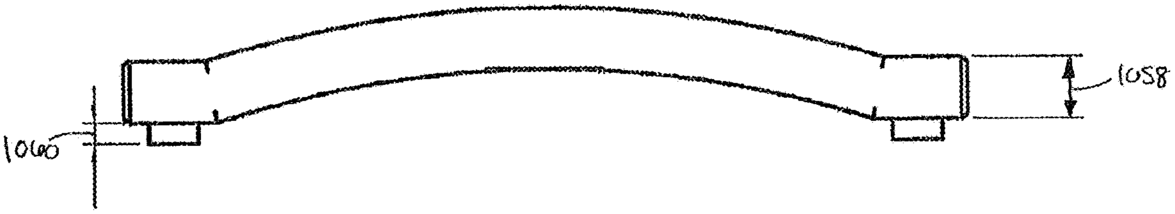
FIG. 15B provides exemplary dimensions of the faceplate of FIG. 5B.

FIG. 15B provides exemplary dimensions of the faceplate of FIG. 5B. As shown the at least one cushion (seen at 160 of FIG. 5B) can comprise a height 1060 of about 2 mm. The end section (seen at 156 of FIG. 5B) can comprise a height 1058 of about 6 mm.

Figure 15C:
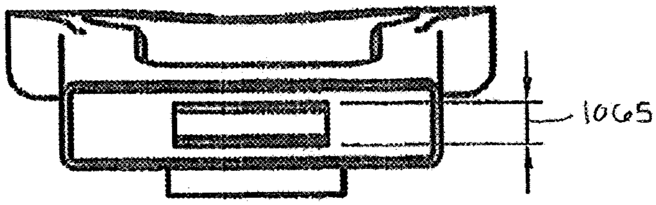
FIG. 15C provides exemplary dimensions of the faceplate of FIG. 5C.

FIG. 15C provides exemplary dimensions of the faceplate of FIG. 5C. In certain embodiments, the portion of the tracheostomy tie channel (seen at 155 of FIG. 5C) that exits on a side surface of the end section comprises a height 1065 of about 3 mm.

Figure 16A:
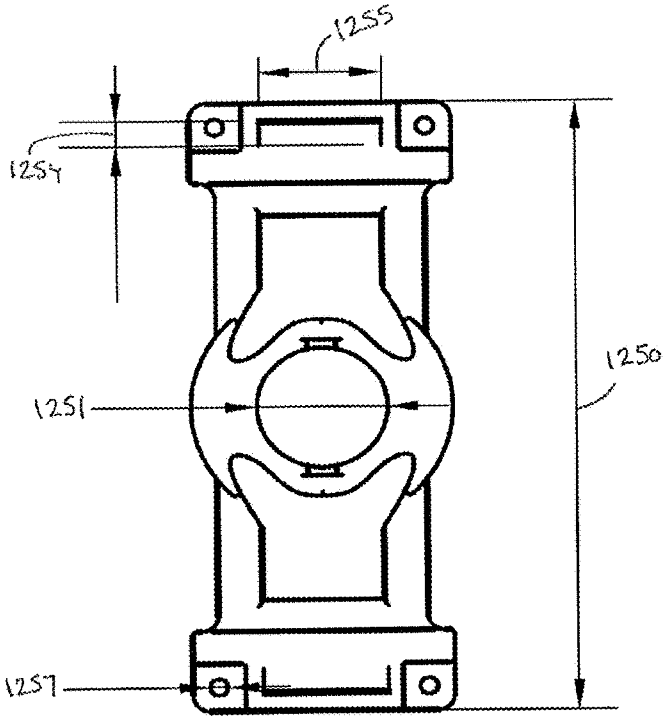
FIG. 16A provides exemplary dimensions of the faceplate of FIG. 9A.

FIG. 16A provides exemplary dimensions of the faceplate of FIG. 9A. The length 1250 of this embodiment can be about 76 mm. The cannula receiving portion (seen at 251 of FIG. 9A) can comprise a diameter of about 15 mm. In certain embodiments, the tracheostomy tie channel (seen at 255 of FIG. 9A), when viewed from the top comprises an opening with a width 1255 of about 14 mm, a length 1254 of about 3.25 mm, or a combination thereof. In one embodiment, at least one suture opening (seen at 257 of FIG. 9A) comprises a diameter of about 2 mm.

Figure 16B:
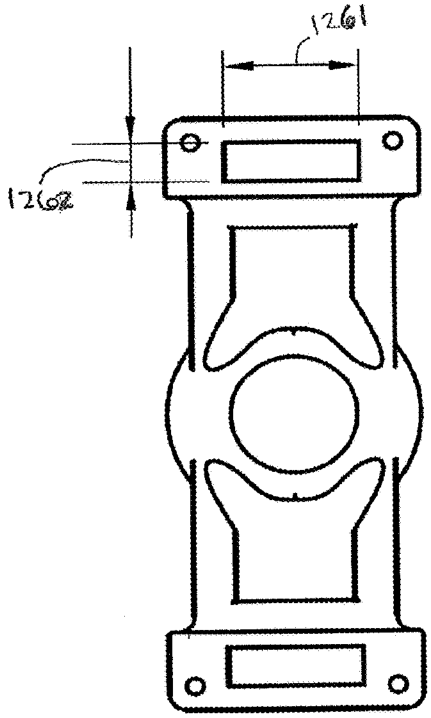
FIG. 16B provides exemplary dimensions of the faceplate of FIG. 9B.

FIG. 16B provides exemplary dimensions of the faceplate of FIG. 9B. In the pictured embodiment, the cushion inset (seen at 261 of FIG. 9B), comprises a width 1261 of about 16 mm, a length 1262 of about 5 mm, or a combination thereof.

Figure 9C:
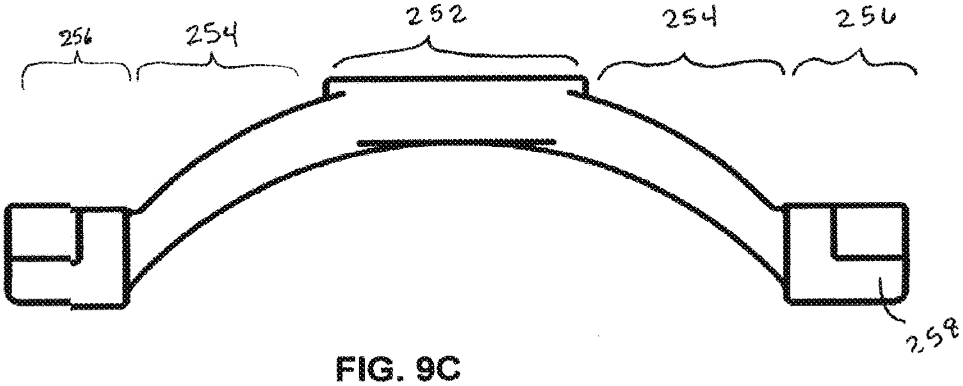
FIG. 9C provides a side view of the FIG. 9A embodiment.
Figure 16C:
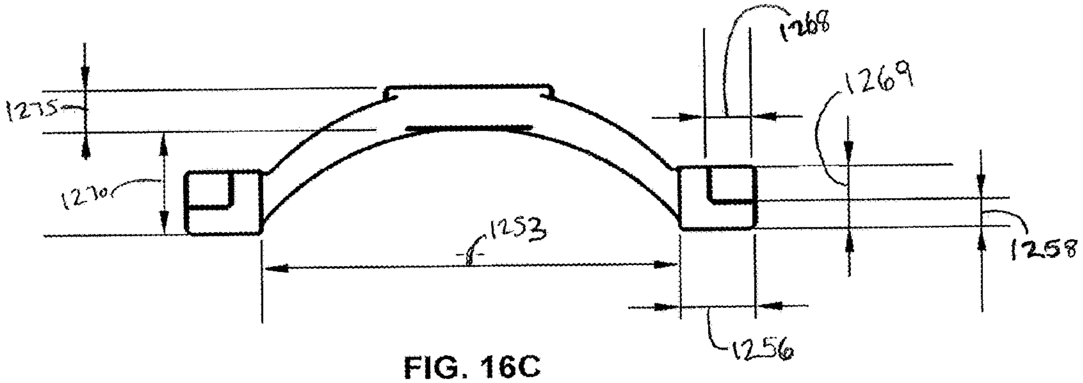
FIG. 16C provides exemplary dimensions of the faceplate of FIG. 9C.

FIG. 16C provides exemplary dimensions of the faceplate of FIG. 9C. In embodiments, the area comprising the two linking sections (seen at 254 of FIG. 9C) and central portion (seen at 252 of FIG. 9C) comprises a length 1253 of about 60 mm. The end section (seen at 256 of FIG. 9C) can comprise a length 1256 of about 10 mm and a height 1069 of about 6 mm. The portion of the footplate (seen at 258 of FIGS. 9A-9C) correlating to the recessed portion (seen at 268 of FIG. 9A) can comprise a height 1258 of about 4 mm. The recessed portion can comprise a length 1268 of about 6 mm. The creep space height 1270 can be about 15 mm. In embodiments, the central portion can comprise a thickness 1275 of about 6 mm.

Figure 17A:
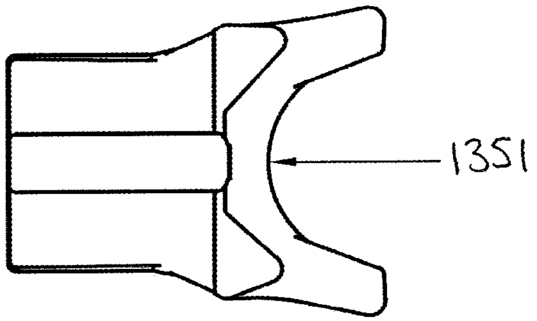
FIG. 17A provides exemplary dimensions of the sponge of FIG. 11D.

FIG. 17A provides exemplary dimensions of the sponge of FIG. 11D. As shown, the cannula receiving portion (seen at 351 of FIG. 11D) can comprise a radius of curvature 1351 that is about 7.5 mm.

Figure 17B:
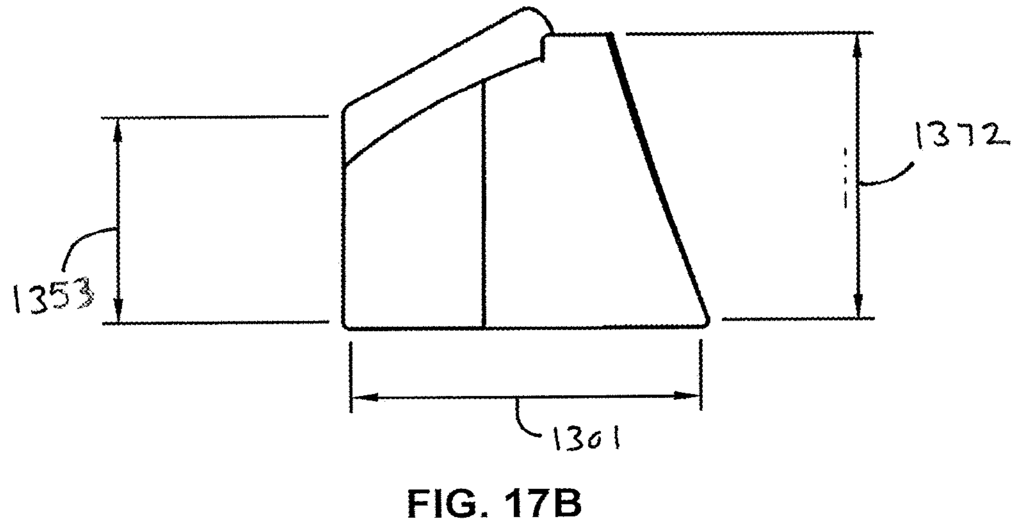
FIG. 17B provides exemplary dimensions of the sponge of FIG. 11E.

FIG. 17B provides exemplary dimensions of the sponge of FIG. 11E. The front surface (seen at 372 of FIG. 11E) of the pictured embodiment can comprise a height 1372 of about 20.5 mm. The back surface of the sponge can comprise a height 1353 of about 15 mm. The bottom surface (seen at 371 of FIG. 11E) can comprise a length of about 23 mm.

Figure 17C:
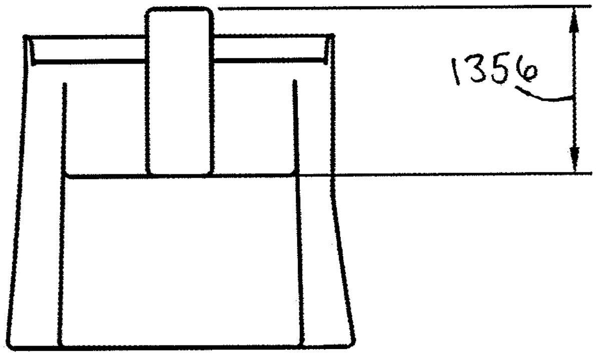
FIG. 17C provides exemplary dimensions of the sponge of FIG. 11F.

FIG. 17C provides exemplary dimensions of the sponge of FIG. 11F. The handle (seen at 356 of FIG. 11F) can comprise a height 1356 of about 11 mm.

In alternative embodiments, such as those disclosed in FIGS. 13B and 13C, the wound dressing material 700, 800 comprises a single piece of material with protrusions 754, 854 that extend downward. Embodiments such as these can be placed over the top surface of the faceplate, and the protrusions 754, 854 extend downward through the viewing ports to contact the skin and serve as wound dressing material. In such embodiments, the undersurface of the sponge 700, 800 can be coated with an adhesive to assist with securing the wound dressing material into place on the top surface of the faceplate.

Figure 18A:
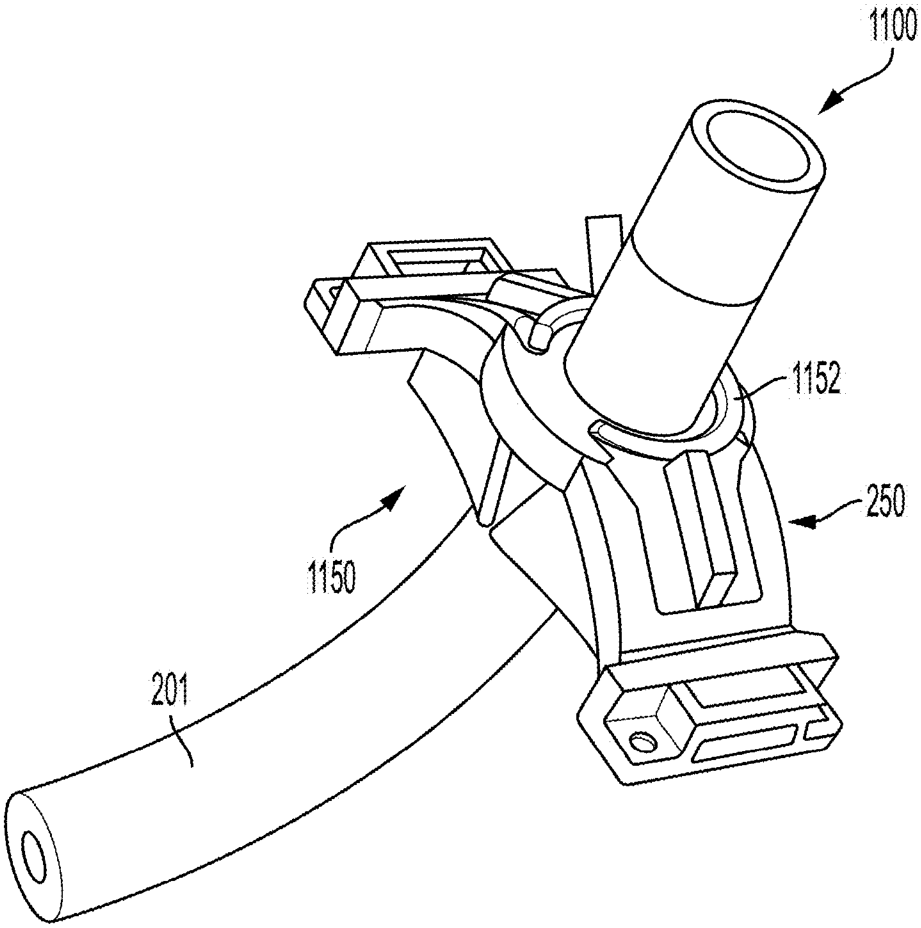
FIG. 18A shows a top perspective view of a tall faceplate secured to an outer tracheostomy cannula that includes an alternate wound dressing material. The wound dressing material can be seen as a single sponge residing primarily in the space underneath the faceplate with a C-shaped connector surrounding the cannula and extending across a section of the faceplate.
Figure 18B:
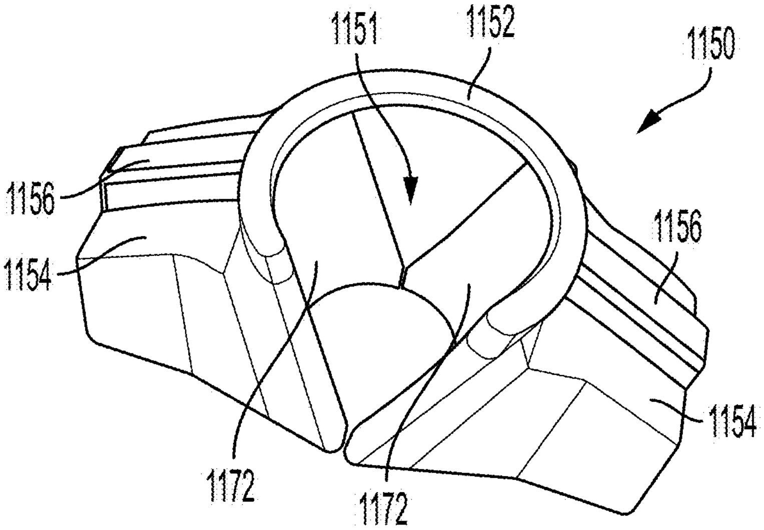
FIG. 18B provides a detailed top perspective view of the single sponge shown in FIG. 18A.

FIG. 18A provides an additional embodiment of the tracheostomy accessory system 1100 disclosed herein, and a detailed view of the single sponge embodiment 1150 is shown in FIG. 18B. The embodiment includes a tall faceplate 250, a cannula 201, and a wound dressing material in the form of a single sponge 1150 with two absorbent sections 1154 connected via a C-shaped connecting member 1152 that rests on a portion of the top surface of faceplate 250 and partially encircles the cannula 201. Each of the absorbent sections 1154 includes an optional extension or handle 1156 extending from its top surface, and a cannula receiving portion 1151 exists between the opposite inner surfaces 1172 of the absorbent sections 1154. In embodiments, there can exists an adhesive on least a portion of the bottom of the sponge 1150 that can be peeled off. The adhesive can be disposed on the bottom surface of the absorbent sections 1154 such that, in operation, the adhesive reversibly secures the sponge to the skin of the patient. Further, a bottom surface of the connecting member 1152 can comprise an adhesive that assists in securing the connecting member 1152 to the top face of the faceplate 250.

The stoma viewports 153, 253 as shown in the various exemplary embodiments provide substantial advantages over traditional tracheostomy faceplates or flanges. One advantage includes providing an unobstructed view of the stoma during placement of the tracheostomy and associated accessories. Traditional tracheostomy faceplates lack a stoma viewport, and, as a result, during placement of the tracheostomy, there is a moment when the surgeon or health care provider cannot see the stoma or hole into which the tube is being inserted. The presently disclosed tracheostomy accessory overcomes this disadvantage by inclusion of the stoma viewports 153, 253, which permit a continuous view of the stoma during the implantation procedure. Additionally, the stoma viewports 153, 253 allow for dressing changes that are easier to perform and reduce patient discomfort. As seen in FIGS. 1A-1C, when using traditional tracheostomy faceplates dressing can only be placed or removed by inserting the material between the flange and the skin. The combination of the view ports 153, 253 and elevated faceplate designs 150, 250 that are disclosed herein allow for easier insertion of a wound dressing (due to creep space or the ability to insert the dressing through the viewport 153, 253) and the use of custom dressing material (300, 400, 600, 700, 800, & 1150 of FIGS. 10-13 and 18) to avoid the necessity of forcing the sponge between the skin and flange.

Further, the designs disclosed herein 150, 250 permit the opportunity for improved care of the stoma. By way of example, the stoma viewports 153, 253 allow for suction of secretions, cleaning of wound, control of bleeding, cauterization of the stomal wound, or a combination thereof without the need to remove the tracheostomy or any accessory attached thereto. This represents a significant advantage of traditional tracheostomy with a solid flanges (FIGS. 1A-1C), wherein such activities can require complete removal of the tracheostomy tube, which is a potentially dangerous event i.e. one could lose a stable airway.

The wound dressing material 300, 400, 600, 700, 800 can comprise various substances that are appropriate for absorbing drainage from a wound. The wound-packing material can comprise hydrophilic materials. In one embodiment, the wound-packing material comprises a polyvinyl alcohol (PVA) sponge.

Another aspect of the present invention includes a method of using the tracheostomy accessory in accordance with any embodiment disclosed within this specification or otherwise apparent from the descriptions herein. In embodiments, a cannula is inserted into a stoma opening and a faceplate in accordance with any one or more of the embodiments disclosed herein is placed around the cannula and secured to the patient. The faceplate can be secured to the patient via sutures, tracheostomy straps or ties, or a combination thereof. Wound dressing material can be placed with in the creep space between the faceplate and the skin of the patient.

In certain embodiments, the wound dressing material is placed through a stoma viewport until the wound dressing material contacts the skin of the patient. Certain embodiments comprise changing of the wound dressing material, wherein the wound dressing material is removed through the stoma viewport and new wound dressing material is inserted through the stoma viewport.

Also disclosed is a kit that includes a faceplate in accordance with any embodiment disclosed within this specification or otherwise apparent from the descriptions herein. In embodiments, the kit comprises the faceplate and instructions for use or assembly of the tracheostomy accessory. The instructions can be physically provided with the kit or accessible separately from the kit, such as via the retailer's or manufacturer's website. The kit can include a cannula. In alternate embodiments, the kit does not include a cannula. In certain embodiments, the wound dressing material is included with the kit.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

The disclosed technology centers around design and functional improvements associated with the use of a tracheostomy tube, a commonly used device for creation of a temporary or permanent breathing passage.

Flange Design: Current flanges have several problems including the following:

1. They do not have any creep space between the flange and skin to allow easy insertion of padding or gauze to absorb trach secretions and also do not conform to the neck of the patient i.e. it's one flange for all;
2. No specific holes are created to put sutures into further secure the tube;
3. The trach flanges often bury into the skin of the patient and create wounds—these are extremely painful and also when an attempt is made to put a gauze or pad between the flange and skin, it can be very painful to the patient Currently available flange lacks a space for receiving ties or sutures (see FIG. 1) and there is no way to access trach wounds and place gauze or a pad. (See FIGS. 2A-2B).

The present invention can include hooks, rings, or fenestrations 157, 257 for receiving trach sutures, leaving the port for trach ties open. (See FIG. 14).

The presently disclosed tracheostomy accessory can include fenestrate flanges than allows inspection and placement of wound dressing material (FIG. 14). This arrangement avoids the necessity of pushing gauze between the trach flange and the skin of a patient. The tracheotomy accessory can also be supplied with custom sponges 600, 390 that serve as wound dressing material (FIG. 14).

Example 2

Minimal Impact Dual Access Tracheostomy Faceplate

Background:

There has been an increasing emphasis on quality improvement in terms of health care delivery globally and especially in the United States. For example, preventing hospital acquired injuries like tracheostomy associated pressure ulcers (TRAPUS) has a significant impact on hospital stay, infection control, quality of care and patient experience. Tracheostomy is a common procedure, often lifesaving, and is performed more to help more than 100,000 patients ever year. Inability to properly care of tracheostomy wounds, shear forces, pressure on the skin and moisture all impact the tracheostomy wound and consequently its care.

The "minimal impact dual access tracheostomy faceplate" disclosed herein was a consequence of clinical observation where design modifications have been made to reduce the impact of constant contact, moisture and access to the tracheostomy site—in a way that improves the ability of health care professional to care for these wounds due to better visibility of the tracheostomy opening and access to make easy dressing changes without causing drag and stress on the tracheostomy wound. These designs also improve quality of patient care by reducing the pain and discomfort associated with aggressive dressing changes, pressure ulcers and lack of ability to inspect and care for the wound which is seen with current tracheostomy designs Main Base Plate Curvature:

The curvature of the main base plate was adjusted to give a central elevation to allow minimal contact of the faceplate to the skin. This had a dual purpose (see FIGS. 4A-4C):

1. As mentioned, the elevation prevented the contact of the face plate to the central portion of the neck which usually has an uneven surface due to the attachment of the sternocleidomastoid muscles and the depression of the supraclavicular fossa. The unevenness, with a normal base plate, creates the opportunity for friction, pressure and pressure ulcers. Moving the contact point away will reduce the possibility of pressure ulcers and wounds in this area. Given the central portion of the tracheostomy footplate i.e. in the region of the tracheostomy tube is also the access point for tracheostomy care such as dressing changes, avoidance of ulcers is not only helpful in tracheostomy wound care but also makes this less painful to the patient 2. The second advantage of elevation of the tracheostomy faceplates it to allow ease of change of dressings making it easier for nurses and respiratory therapist to change tracheostomy dressings.

Dual Access (Stomal View) Port:

The creation of windows on either side of the tracheostomy tube with a curvature towards the tube was intentionally designed to provide several advantages with respect to tracheostomy care and placement.

1. During tracheostomy tube placement as the tube is placed in the tracheostomy stoma, there is a split-second when the healthcare professional inserting the tube loses view of the opening created in the trachea—this is often compounded by the fact that the faceplate of the tracheostomy blocks the view of the tracheostomy tube entering the opening creating on the tracheal wall. The dual ports will allow superior viewing and vantage point to be able to minimize and possibly eliminate this split second loss of surgical view during tracheostomy tube placement.
2. Once the tracheostomy tube is in place, especially during the first few days after the procedure, the wound tends to create excessive secretions and can also be complicated by bleeding. Prior port-less opaque tracheostomy faceplates do not allow for inspection of the tracheostomy tube insertion site to help manage minor bleeding or inspect the wound.
3. Custom sponges that will fit within the dual stomal view ports will not only provide additional stability to the minimal impact dual access tracheostomy footplate, but also help ease of dressing changes through the access ports or stomal view ports.

Tracheostomy Flange with Tracheostomy Tie Openings, Skin Fixation Suture Openings and Protective Cushion Inserts/Cushion Sleeves:

The ends of the tracheostomy footplate or the flange has been specially designed to serve multiple functions.

1. The flat ends with adequate extension allow an adequate foot print to create a stable footplate design. The design synchronizes with the tracheostomy cannula to provide a tripod support to the structure and stability to the overall design
2. The flange also includes a flat or step tracheostomy tie insertion openings. The stepped design prevents the Velcro ties touching the skin (also a known cause of pressure ulcers) (see FIG. 7B).
3. Two opening for suturing the tracheostomy are designed so that surgeon while placing a new tracheostomy do not have to force a suture through the flange of the tube; a surgical maneuver that can sometimes lead to inadvertent injury to the surgeon or assistant. Pre-fashion holes make suture placement and removal easier.
4. Protective cushion inserts and protective sleeves (seen at 458 of FIG. 14) custom designed to fit on to the base of the flange of the footplate are efforts are reducing pressure ulcers and minimizing trauma to the skin.

Base Plate Extension:

This extension of the base place to encircle the tracheostomy tube and extend outwards was designed to provide stability to the footplate design and strengthen structure of the footplate arch that is compromised by the presence of the dual stomal view ports. This is an intentional and anticipatory design decision to ensure structural integrity.

Outer Cannula Opening and Swivel Adapter:

The outer cannula opening accommodates standard outer cannula design and the swivel adapter allows for placement of the outer cannula in the minimal access dual access port foot plate in a manner similar to current tracheostomy designs. This swivel function will allow micro-adjustments of the tracheostomy cannula and footplate as a unit with patient movement and help minimize friction and stress ulcers.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. A tracheostomy accessory comprising:

a faceplate that comprises a central portion, at least two end sections, and at least two linking sections, wherein the at least two linking sections are configured to connect the central portion to the end sections;

the central portion being elevated in relation to the end sections such that contact between the faceplate and the skin of a patient is reduced;

each of the at least two end sections comprising a footplate configured to support the faceplate on the patient;

the faceplate further comprising a canula receiving portion that comprises a channel extending through the central portion, wherein the canula receiving portion is configured to receive and hold at least a portion of a tracheostomy canula, wherein the at least two linking sections each comprise a stomal viewport; and a sponge, wherein at least a portion of the sponge is configured to pass through a first stomal viewport of the at least two linking sections and wherein a first face of the sponge comprises an outer contour matching a contour of the first stomal viewport, whereby the sponge is configured to removably reside at least partially within the first stomal viewport in a deployed state.

2. The tracheostomy accessory of claim 1, wherein the at least two linking sections comprise a curvature that extends upward from the end sections and terminates at the central portion to create an arched faceplate.

3. The tracheostomy accessory of claim 2, wherein the at least two linking sections comprise a mean angle of curvature of about 125 degrees or about 161 degrees.

4. The tracheostomy accessory of claim 1, wherein the central portion is integral with the at least two linking sections and each linking section is integral with one end section such that the faceplate comprises a single, continuous structure.

5. The tracheostomy accessory of claim 1, wherein the stomal viewports are configured to permit viewing of a stoma on the patient.

6. The tracheostomy accessory of claim 5, wherein the sponge is configured to reside within a space between the skin of the patient and at least one of the at least two linking sections of the faceplate.

7. The tracheostomy accessory of claim 1, wherein the sponge comprises a protrusion for use in positioning the sponge through the first stomal viewport..

8. The tracheostomy accessory of claim 7, wherein the sponge is configured to reside a space between the first stomal viewport and the skin of the patient.

9. The tracheostomy accessory of claim 8, wherein an undersurface of the sponge comprises an adhesive material configured to reversibly secure the sponge to the skin of the patient.

10. The tracheostomy accessory of claim 1, wherein each footplate further comprises at least one cushion configured to reduce irritation of the patient's skin.

11. The tracheostomy accessory of claim 1, wherein the faceplate further comprises at least one hole that is configured to receive and hold a suture.

12. The tracheostomy accessory of claim 11, wherein the at least one hole is disposed on at least one of the footplates.

13. The tracheostomy accessory of claim 1, wherein the faceplate further comprises at least one tie channel through which a tracheostomy tie or strap can be passed and used to secure the faceplate to the neck of the patient.

14. The tracheostomy accessory of claim 1, wherein the faceplate comprises a medical grade metal, a medical-grade polymer, or a combination thereof.

15. The tracheostomy accessory of claim 14, wherein the medical grade metal comprises stainless steel, titanium, tantalum, gold, platinum, palladium, or a combination thereof.

16. The tracheostomy accessory of claim 14, wherein the faceplate comprises a silicone elastomer, sterilizable plastic, polytetrafluoroethylene, polyether block amide, polyvinyl chloride or a combination thereof.

17. The tracheostomy accessory of claim 1, wherein the faceplate is reusable.

18. The tracheostomy accessory of claim 1, wherein the faceplate comprises a height from about 3 mm to about 20 mm.

19. The tracheostomy accessory of claim 1, wherein the faceplate comprises a height of about 5 mm or about 15 mm.

20. The tracheostomy accessory of claim 1, wherein a second, arcuate face of the sponge is configured to surround at least a portion of the tracheostomy canula in the deployed state.

21. A method of stabilizing a tracheostomy canula in a patient comprising:

obtaining the tracheostomy accessory of claim 1;

placing the tracheostomy canula through the canula receiving portion of the faceplate; and securing the faceplate to the patient.

22. A kit for use in stabilization of a tracheostomy tube comprising:

the tracheostomy accessory of claim 1; and instructions for use of the kit.

* * * * *